United States Patent
Pevarello et al.

(10) Patent No.: US 10,669,267 B2
(45) Date of Patent: Jun. 2, 2020

(54) SUBSTITUTED N-[2-(4-PHENOXYPIPERIDIN-1-YL)-2-(1,3-THIAZOL-5-YL)ETHYL]BENZAMIDE AND N-[2-(4-BENZYLOXYPIPERIDIN-1-YL)-2-(1,3-THIAZOL-5-YL)ETHYL]BENZAMIDE DERIVATIVES P2X7 RECEPTOR ANTAGONISTS

(71) Applicant: Axxam S.P.A., Bresso (MI) (IT)

(72) Inventors: Paolo Pevarello, Bresso (IT); Adolfo Prandi, Bresso (IT)

(73) Assignee: Axxam S.P.A., Bresso (MI) (IT)

( * ) Notice: Subject to any disclaimer, the term of this patent is extended or adjusted under 35 U.S.C. 154(b) by 0 days.

(21) Appl. No.: 16/327,854

(22) PCT Filed: Aug. 9, 2017

(86) PCT No.: PCT/EP2017/070163
§ 371 (c)(1),
(2) Date: Feb. 25, 2019

(87) PCT Pub. No.: WO2018/041563
PCT Pub. Date: Mar. 8, 2018

(65) Prior Publication Data
US 2019/0194180 A1    Jun. 27, 2019

(30) Foreign Application Priority Data
Aug. 31, 2016 (EP) ..................... 16186655

(51) Int. Cl.
C07D 417/00 (2006.01)
C07D 417/02 (2006.01)
(Continued)

(52) U.S. Cl.
CPC ......... *C07D 417/02* (2013.01); *C07D 417/06* (2013.01); *C07D 417/14* (2013.01);
(Continued)

(58) Field of Classification Search
CPC ........ C07D 417/02; A61P 25/00; A61P 27/02; A61P 21/00; A61P 29/00
(Continued)

(56) References Cited

FOREIGN PATENT DOCUMENTS

WO    2015118019 A1    8/2015

OTHER PUBLICATIONS

Silverman, The Organic Chemistry of Drug Design and Drug Action, Academic Press., Inc. 1992, p. 19-20. (Year: 1992).*
(Continued)

*Primary Examiner* — Taylor V Oh
(74) *Attorney, Agent, or Firm* — Silvia Salvadori, P.C.; Silvia Salvadori

(57) ABSTRACT

The present invention relates to novel substituted phenoxy- and benzyloxy-piperidine compounds of formula (I) having P2X7 receptor (P2X7) antagonistic properties, pharmaceutical compositions comprising these compounds, chemical processes for preparing these compounds and their use in the treatment or prophylaxis of diseases associated with P2X7 receptor activity in animals, in particular humans.

(I)

(Continued)

7 Claims, 1 Drawing Sheet

(51) Int. Cl.
| | |
|---|---|
| *C07D 417/06* | (2006.01) |
| *C07D 417/14* | (2006.01) |
| *A61P 27/02* | (2006.01) |
| *A61P 21/00* | (2006.01) |
| *A61P 25/00* | (2006.01) |
| *A61P 29/00* | (2006.01) |

(52) U.S. Cl.
CPC ............... *A61P 21/00* (2018.01); *A61P 25/00* (2018.01); *A61P 27/02* (2018.01); *A61P 29/00* (2018.01)

(58) Field of Classification Search
USPC .............................................. 546/269, 269.7
See application file for complete search history.

(56) References Cited

OTHER PUBLICATIONS

International Preliminary Report on Patentability of PCT/EP2017/070163 dated Aug. 29, 2018.
Notification of receipt of demand by competent International Preliminary Examining authority for PCT/EP2017/070163 dated Jun. 19, 2018.
Reply to written opinion of PCT/EP2017/070163 dated Jun. 11, 2018.
Search Report and Written Opinion of PCT/EP2017/070163 dated Oct. 25, 2017.
Second Written Opinion of PCT/EP2017/070163 dated Jul. 16, 2018.

* cited by examiner

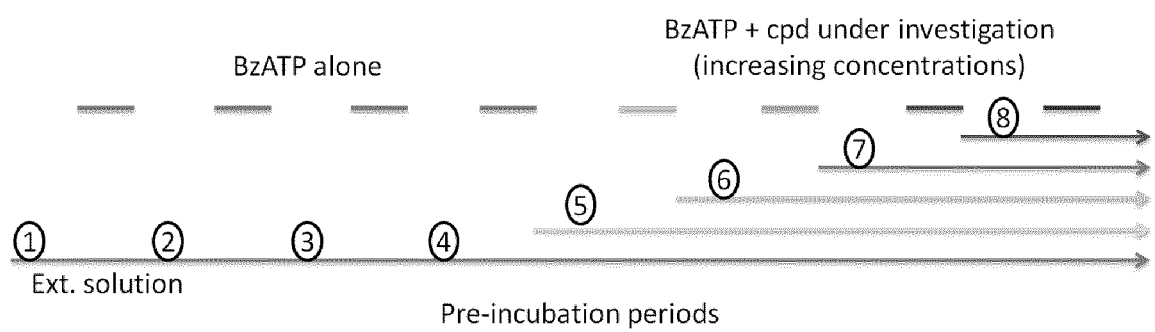

SUBSTITUTED N-[2-(4-PHENOXYPIPERIDIN-1-YL)-2-(1,3-THIAZOL-5-YL)ETHYL]BENZAMIDE AND N-[2-(4-BENZYLOXYPIPERIDIN-1-YL)-2-(1,3-THIAZOL-5-YL)ETHYL]BENZAMIDE DERIVATIVES P2X7 RECEPTOR ANTAGONISTS

This application is a U.S. national stage of PCT/EP2017/070163 filed on Aug. 9, 2017, which claims priority to and the benefit of European Application No. 16186655.3 filed on Aug. 31, 2016, the contents of which are incorporated herein by reference in their entireties.

The present invention is related to novel substituted phenoxy- and benzyloxy-piperidine compounds of formula (I) having P2X7 receptor (P2X7) antagonistic properties, pharmaceutical compositions comprising these compounds, chemical processes for preparing these compounds and their use in the treatment or prophylaxis of diseases associated with P2X7 receptor activity in animals, in particular humans.

P2X7 belongs to the family of P2X ionotropic receptors. P2X7 is activated by extracellular nucleotides, notably adenosine triphosphate (ATP). P2X7 is distinguished from other P2X family members by the specific localization (CNS and immunocompetent cells in particular), by the high concentrations of ATP (in the mM range) required to activate it and by its ability to form a large pore upon prolonged or repeated stimulation. P2X7 is a ligand-gated ion channel and is present on a variety of cell types, largely those known to be involved in the inflammatory and/or immune process, specifically, macrophages, mast cells and lymphocytes (T and B). Activation of the P2X7 receptor by extracellular nucleotides, e.g., ATP, leads to the release of interleukin-β (1L-1β) and giant cell formation (macrophages/microglial cells), degranulation (mast cells) and L-selectin shedding (lymphocytes). P2X7 receptors are also located on antigen-presenting cells (APC), keratinocytes, salivary acinar cells (parotid cells), hepatocytes, erythrocytes, erythroleukaemic cells, monocytes, fibroblasts, bone marrow cells, neurones, and renal mesangial cells. The P2X7 receptor is also known to be a pain sensor in the nervous system. Experiments using P2X7 deficient mice demonstrate the role of P2X7 in the development of pain as these mice were protected from the development of both adjuvant-induced inflammatory pain and partial nerve ligation induced neuropathic pain. There is also growing evidence that P2X7 or its downstream effectors, such as IL-1β, are involved in the pathophysiology of several neurological disorders, such as, Alzheimer's Disease (J. I. Diaz-Hernandez et al., Neurobiol. Aging 2012, 1816-1828: In vivo P2X7 inhibition reduces Aβ plaques in AD through GSK3β). P2X7 is thought to have an important function in neurotransmission within the CNS through its activation on postsynaptic and/or presynaptic neurons and glia. Data has emerged using in situ hybridization that P2X7 receptor mRNA is widely distributed throughout the rat brain. Specifically, areas of high P2X7 mRNA expression were found in the anterior olfactory nucleus, cerebral cortex, piriform cortex (Pir), lateral septal nucleus (LS), hippocampal pyramidal cell layers of CA1, CA3, CA4, pontine nuclei, external cuneate nucleus, and medial vestibular nucleus. P2X7 hybridization signals were also observed in the motor neurons of the trigeminal motor nucleus, facial nucleus, hypoglossal nucleus, and the anterior horn of the spinal cord.

Hence there is a therapeutic rationale for the use of P2X7 antagonists in the treatment of a variety of disease states. These states include but are not limited to diseases associated with the CNS such as Alzheimer's Disease, Parkinson's Disease, Huntington's Disease, Amyotrophic Lateral Sclerosis, spinal cord injury, cerebral ischemia, head trauma, meningitis, sleep disorders, mood and anxiety disorders, HIV-induced neuroinflammation, and chronic neuropathic and inflammatory pain. Furthermore, peripheral inflammatory disorders and autoimmune diseases including but not limited to rheumatoid arthritis, ostheoarthritis, psoriasis, allergic dermatitis, asthma, chronic obstructive pulmonary disease, airways hyper-responsiveness, septic shock, bronchitis, glomerulonephritis, irritable bowel syndrome, fatty liver disease, liver fibrosis, skin injury, lung emphysema, muscular dystrophy, fibrosis, atherosclerosis, burn injury, Crohn's Disease, ulcerative colitis, age-related macular degeneration, growth and metastasis of malignant cells, Sjögren's syndrome, myoblastic leukaemia, diabetes, osteoporosis, ischemic heart disease are all examples where the involvement of P2X7 receptors has been implicated. In view of the clinical importance of P2X7, the identification of compounds that modulate P2X7 receptor function represents an attractive avenue into the development of new therapeutic agents.

P2X7 inhibitors are described in various patent applications such as:

WO2004/099146 that discloses benzamide inhibitors of the P2X7 receptor and their use in the treatment of inflammatory diseases.

WO2009/108551 that discloses heteroarylamide analogs and their use in P2X7 receptor mediated conditions.

WO2009/132000 that discloses quinoline and isoquinoline substituted P2X7 receptor antagonists and their use in P2X7 receptor mediated conditions.

WO2015/119018 that discloses thiazole and oxazole derivatives as P2X7 receptor antagonists and their use in P2X7 receptor mediated conditions.

However there is still an unmet need for compounds which are able to efficiently antagonize P2X7 and that can be delivered in the different target organs which are sites of a P2X7 mediated pathology, including the brain. Such compounds are provided herein.

Various embodiments of the invention are presented hereafter;

The present invention relates to thiazole compounds of the following formula (I) or a pharmaceutically acceptable salt thereof:

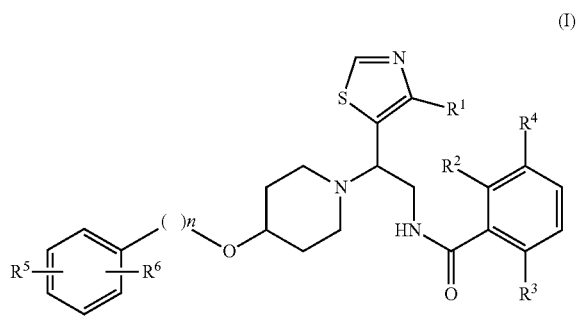

(I)

including any stereochemically isomeric form thereof, wherein n is 0 or 1;

$R^1$ is C 1-C4 alkyl (optionally substituted with hydroxyl or halogen), preferably methyl, fluoromethyl, difluoromethyl, trifluoromethyl;

each of $R^2$, $R^3$, and $R^4$ is independently hydrogen, halogen, or the $R^2$ and $R^4$ groups, taken together, form a six membered heterocyclic ring containing a nitrogen atom, provided that at least one of $R^2$, $R^3$, and $R^4$ is not hydrogen;

each of $R^5$ and $R^6$ is hydrogen or halogen provided that at least one of $R^5$ and $R^6$ is halogen;

As used in the foregoing definitions:

The terms "halo", "halogen" and "halide", which may be used interchangeably, refer to a substituent fluoro, chloro, bromo, or iodo.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration.

Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, trifluoromethanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

A preferred embodiment of the invention relates to compounds of Formula (I) as defined above wherein:

n is 0 or 1;

$R^1$ is methyl, or difluoromethyl;

each of $R^2$, $R^3$, and $R^4$ independently is hydrogen, fluorine, chlorine or the $R^2$ and $R^4$ groups, taken together, form a six membered heterocyclic ring containing a nitrogen atom provided that at least one of $R^2$, $R^3$, and $R^4$ is not hydrogen;

each of $R^5$ and $R^6$ is hydrogen, fluorine or chlorine provided that at least one of $R^5$ and $R^6$ is halogen;

Another embodiment of the invention relates compounds of Formula (I) as defined above wherein:

n is 0 or 1;

$R^1$ is methyl, or difluoromethyl;

each of $R^2$, $R^3$, and $R^4$ independently is hydrogen, fluorine or chlorine, provided that at least one of $R^2$, $R^3$, and $R^4$ is not hydrogen;

each of R5 and $R^6$ is hydrogen, fluorine or chlorine provided that at least one of $R^5$ and $R^6$ is halogen;

Another embodiment of the invention relates compounds of Formula (I) as defined above wherein:

n is 0 or 1;

$R^1$ is methyl, or difluoromethyl;

$R^3$ is hydrogen and the $R^2$ and $R^4$ groups, taken together, form a six membered heterocyclic ring, wherein the six membered heterocyclic ring togheter the phenyl group form a quinoline ring.

Most preferably, a compound of formula (I) according to this invention is selected from the group consisting of:

| Compound | IUPAC Name |
|---|---|
| 1 | 2-chloro-6-fluoro-N-(2-{4-[(4-fluorophenyl)methoxy]piperidin-1-yl}]-2-(4-methyl-1,3-thiazol-5-yl)ethyl)benzamide |
| 2 | 2-chloro-N-(2-{4-[(4-chlorophenyl)methoxy]piperidin-1-yl}-2-(4-methyl-1,3-thiazol-5-yl)ethyl)-6-fluorobenzamide |
| 3 | 2-chloro-6-fluoro-N-(2-{4-[(3-fluorophenyl)methoxy]piperidin-1-yl}-2-(4-methyl-1,3-thiazol-5-yl)ethyl)benzamide |
| 4 | 2-chloro-6-fluoro-N-(2-{4-[(2-fluorophenyl)methoxy]piperidin-1-yl}-2-(4-methyl-1,3-thiazol-5-yl)ethyl)benzamide |
| 5 | 2-chloro-N-(2-{4-[(3,5-difluorophenyl)methoxy]piperidin-1-yl}-2-(4-methyl-1,3-thiazol-5-yl)ethyl)-6-fluorobenzamide |
| 6 | 2-chloro-N-(2-{4-[(3,4-difluorophenyl)methoxy]piperidin-1-yl}-2-(4-methyl-1,3-thiazol-5-yl)ethyl)-6-fluorobenzamide |
| 7 | 2-chloro-6-fluoro-N-{2-[4-(4-fluorophenoxy)piperidin-1-yl]-2-(4-methyl-1,3-thiazol-5-yl)ethyl}benzamide |
| 8 | 2-chloro-N-{2-[4-(4-chlorophenoxy)piperidin-1-yl]-2-(4-methyl-1,3-thiazol-5-yl)ethyl}-6-fluorobenzamide |
| 9 | 2-chloro-6-fluoro-N-{2-[4-(3-fluorophenoxy)piperidin-1-yl]-2-(4-methyl-1,3-thiazol-5-yl)ethyl}benzamide |
| 10 | 2-chloro-6-fluoro-N-{2-[4-(2-fluorophenoxy)piperidin-1-yl]-2-(4-methyl-1,3-thiazol-5-yl)ethyl}benzamide |
| 11 | 2-chloro-N-{2-[4-(3,5-difluorophenoxy)piperidin-1-yl]-2-(4-methyl-1,3-thiazol-5-yl)ethyl}-6-fluorobenzamide |
| 12 | 2-chloro-N-{2-[4-(3,4-difluorophenoxy)piperidin-1-yl]-2-(4-methyl-1,3-thiazol-5-yl)ethyl}-6-fluorobenzamide |
| 13 | N-(2-{4-[(4-fluorophenyl)methoxy]piperidin-1-yl}-2-(4-methyl-1,3-thiazol-5-yl)ethyl)quinoline-5-carboxamide |
| 14 | N-(2-{4-[(4-chlorophenyl)methoxy]piperidin-1-yl}-2-(4-methyl-1,3-thiazol-5-yl)ethyl)quinoline-5-carboxamide |
| 15 | N-(2-{4-[(3-fluorophenyl)methoxy]piperidin-1-yl}-2-(4-methyl-1,3-thiazol-5-yl)ethyl)quinoline-5-carboxamide |
| 16 | N-(2-{4-[(2-fluorophenyl)methoxy]piperidin-1-yl}-2-(4-methyl-1,3-thiazol-5-yl)ethyl)quinoline-5-carboxamide |
| 17 | N-(2-{4-[(3,5-difluorophenyl)methoxy]piperidin-1-yl}-2-(4-methyl-1,3-thiazol-5-yl)ethyl)quinoline-5-carboxamide |
| 18 | N-(2-{4-[(3,4-difluorophenyl)methoxy]piperidin-1-yl}-2-(4-methyl-1,3-thiazol-5-yl)ethyl)quinoline-5-carboxamide |
| 19 | N-{2-[4-(4-fluorophenoxy)piperidin-1-yl]-2-(4-methyl-1,3-thiazol-5-yl)ethyl}quinoline-5-carboxamide |
| 20 | N-{2-[4-(4-chlorophenoxy)piperidin-1-yl]-2-(4-methyl-1,3-thiazol-5-yl)ethyl}quinoline-5-carboxamide |
| 21 | N-{2-[4-(3-fluorophenoxy)piperidin-1-yl]-2-(4-methyl-1,3-thiazol-5-yl)ethyl}quinoline-5-carboxamide |
| 22 | N-{2-[4-(2-fluorophenoxy)piperidin-1-yl]-2-(4-methyl-1,3-thiazol-5-yl)ethyl}quinoline-5-carboxamide |
| 23 | N-{2-[4-(3,5-difluorophenoxy)piperidin-1-yl]-2-(4-methyl-1,3-thiazol-5-yl)ethyl}quinoline-5-carboxamide |
| 24 | N-{2-[4-(3,4-difluorophenoxy)piperidin-1-yl]-2-(4-methyl-1,3-thiazol-5-yl)ethyl}quinoline-5-carboxamide |
| 25 | 2-chloro-N-{2-[4-(difluoromethyl)-1,3-thiazol-5-yl]-2-{4-[(2-fluorophenyl)methoxy]piperidin-1-yl}ethyl}-6-fluorobenzamide |

| Compound | IUPAC Name |
|---|---|
| 26 | 2-chloro-N-{2[4-(difluoromethyl)-1,3-thiazol-5-yl]-2-{4-[(3,5-difluorophenypmethoxy]piperidin-1-yl}ethyl}-6-fluorobenzamide |
| 27 | 2-chloro-N-{2[4-(difluoromethyl)-1,3-thiazol-5-yl]-2-{4-[(3,4-difluorophenyl)methoxy]piperidin-1-yl}ethyl}-6-fluorobenzamide |
| 28 | 2-chloro-N-{2-[4-(4-chlorophenoxy)piperidin-1-yl]-2-[4-(difluoromethyl)-1,3-thiazol-5-yl]ethyl}-6-fluorobenzamide |
| 29 | 2-chloro-N-{2-[4-(difluoromethyl)-1,3-thiazol-5-yl]-2-[4-(3-fluorophenoxy)piperidin-1-yl]ethyl}-6-fluorobenzamide |
| 30 | 2-chloro-N-{2-[4-(difluoromethyl)-1,3-thiazol-5-yl]-2-[4-(2-fluorophenoxy)piperidin-1-yl]ethyl}-6-fluorobenzamide |
| 31 | 2-chloro-N-{2-[4-(difluoromethyl)-1,3-thiazol-5-yl]-2-[4-(3,5-difluorophenoxy)piperidin-1-yl]ethyl}-6-fluorobenzamide |
| 32 | N-{2-[4-(difluoromethyl)-1,3-thiazol-5-yl]-2-{4-[(2-fluorophenyl)methoxy]piperidin-1-yl}ethyl}quinoline-5-carboxamide |
| 33 | N-{2-[4-(difluoromethyl)-1,3-thiazol-5-yl]-2-{44(3,4-difluorophenyl)methoxy]piperidin-1-yl}ethyl}quinoline-5-carboxamide |
| 34 | N-{2-[4-(difluoromethyl)-1,3-thiazol-5-yl]-2-[4-(4-fluorophenoxy)piperidin-1-yl]ethyl}quinoline-5-carboxamide |
| 35 | N-{2-[4-(4-chlorophenoxy)piperidin-1-yl]-2-[4-(difluoromethyl)-1,3-thiazol-5-yl]ethyl}quinoline-5-carboxamide |
| 36 | N-{2-[4-(difluoromethyl)-1,3-thiazol-5-yl]-2-[4-(3-fluorophenoxy)piperidin-1-yl]ethyl}quinoline-5-carboxamide |
| 37 | N-{2-[4-(difluoromethyl)-1,3-thiazol-5-yl]-2-[4-(2-fluorophenoxy)piperidin-1-yl]ethyl}quinoline-5-carboxamide |
| 38 | N-{2-[4-(difluoromethyl)-1,3-thiazol-5-yl]-2-[4-(3,5-difluorophenoxy)piperidin-1-yl]ethyl}quinoline-5-carboxamide |

Compounds of formula (I) can generally be prepared by reacting a compound of formula (II):

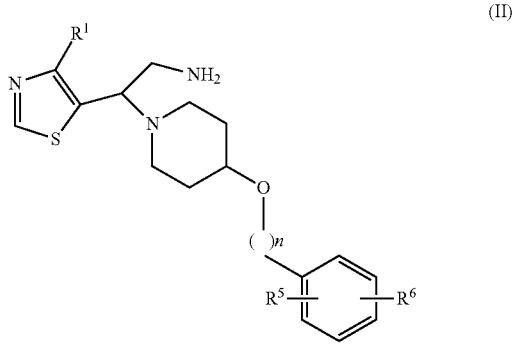

(II)

wherein the meanings of n, $R^1$, $R^5$ and $R^6$ are as defined above, with a compound of formula (III)

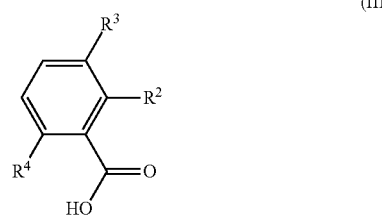

(III)

wherein the meanings of $R^2$, $R^3$ and $R^4$ are as defined above; or with a compound of Formula (Ma):

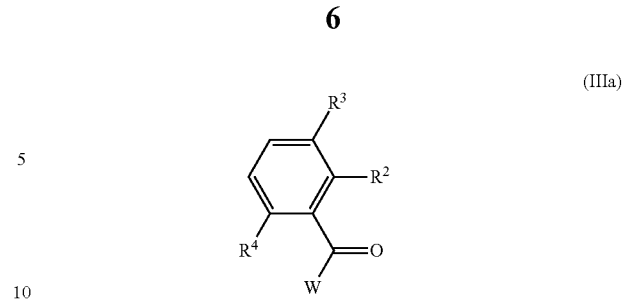

(IIIa)

wherein the meanings of $R^2$, $R^3$ and $R^4$ are as defined above; and W is a suitable leaving group;

and optionally converting the obtained compound of formula (I) into an addition salt thereof, and/or preparing stereochemically isomeric forms thereof.

The reaction of a compound of formula (II) with a compound of formula (III), may be carried out in a at least one reaction-inert solvent and optionally in the presence of at least one suitable coupling reagent and/or a suitable base thereof. It may be convenient to activate the carboxylic acid of formula (III) by adding an effective amount of a reaction promoter. Non-limiting examples of such reaction promoters include carbonyldiimidazole, N,N'-dicyclohexyl-carbodiimide or 1-(3-dimethylaminopropyl)-3-ethylcarbodiimide, hydroxybenzotriazole, benzotriazolyl-oxytris (dimethylamino)-phosphoniumhexafluorophosphate, tetrapyrrolidinophosphoniumhexafluorophosphate, bromotripyrrolidinophosphonium hexafluorophosphate, or a functional derivative thereof, such as disclosed by D. Hudson, (J. Org. Chem. (1988), 53, 617).

W in the compound of Formula (Ma) is an appropriate leaving group such as, for example, halo, e.g. fluoro, chloro, bromo, iodo, or in some instances W may also be a sulfonyloxy group, e.g. methanesulfonyloxy, trifluoromethanesulfonyloxy, benzenesulfonyloxy and the like reactive leaving groups. The reaction of a compound of formula (II) with a compound of formula (III), may be performed in a reaction-inert solvent such as, for example, acetonitrile, dimethyl acetamide, N-methyl-pyrrolidone or DMF, and optionally in the presence of a suitable base such as, for example, sodium carbonate, potassium carbonate or triethylamine. Stirring may enhance the rate of the reaction. The reaction may conveniently be carried out at a temperature ranging between room temperature and the reflux temperature of the reaction mixture.

Compounds of formula (III) and (Ma) are known in the art or can be prepared following the processes reported in the examples.

Compounds of formula (II) can be prepared according to the following scheme:

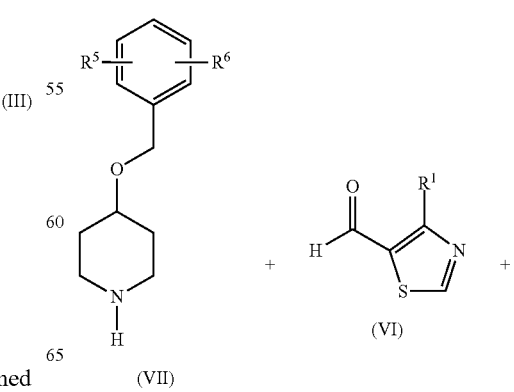

(VII)      (VI)

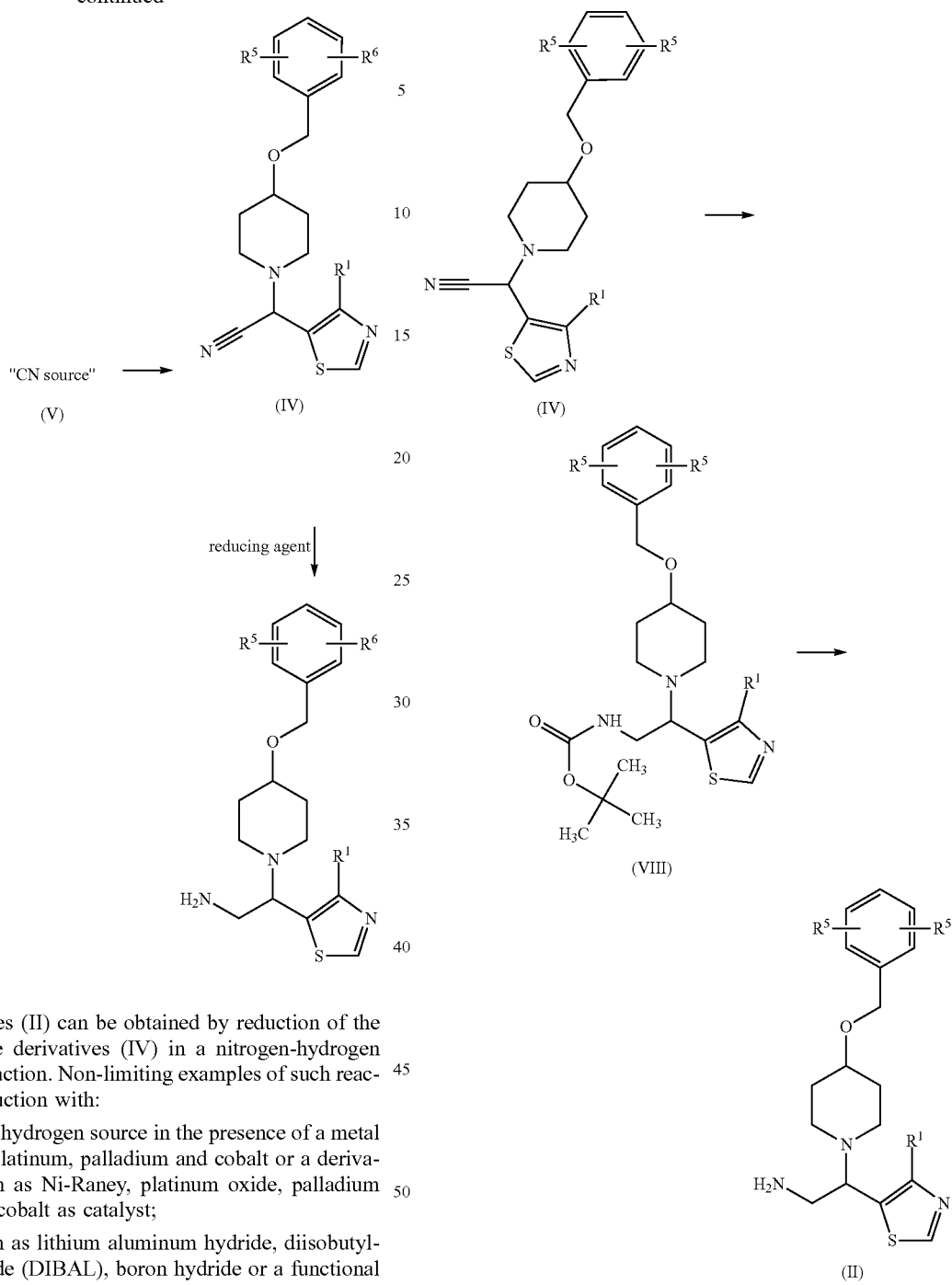

Primary amines (II) can be obtained by reduction of the respective nitrile derivatives (IV) in a nitrogen-hydrogen bond forming reaction. Non-limiting examples of such reaction include reduction with:

hydrogen or a hydrogen source in the presence of a metal such as nickel, platinum, palladium and cobalt or a derivative thereof such as Ni-Raney, platinum oxide, palladium oxide or Raney cobalt as catalyst;

a hydride such as lithium aluminum hydride, diisobutylaluminum hydride (DIBAL), boron hydride or a functional derivative thereof.

The reaction may be performed in a suitable solvent, such as methanol, tetrahydrofuran, acetic acid, diethyl ether, toluene or methanolic ammonia solution preferably at temperatures between −78° C. and RT.

Compounds of formula (IV), wherein $R^1$, $R^5$ and $R^6$ are as defined in formula (I), can be prepared from aldehydes (VI) by a Strecker condensation reaction with the respective heterocyclyl intermediate (VII) in presence of a source of cyanide (V) for example TMSCN or a functional derivative thereof, in a solvent such as AcOH or MeCN, preferably at temperatures between 0° C. and RT.

Alternatively, compounds of formula (II) can also be prepared by a two step procedure as reported above. Reaction of compounds of formula (IV) with a reducing reagent, preferably sodium borohydride in presence of nickel(II) chloride hexahydrate or cobalt(II) chloride hexahydrate and $Boc_2O$ in a solvent such as MeOH, preferably at temperatures between 0° C. and RT, yields the Boc-protected primary amine with formula (VIII). Deprotection with a suitable acid, preferably TFA, gives compounds (II).

Examples of compounds of formula (VI) are represented in the following scheme:

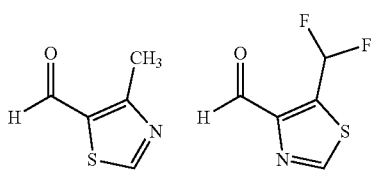

Stirring may enhance the rate of the Strecker condensation reaction. The starting materials and some of the intermediates are known compounds and are commercially available or may be prepared according to conventional reaction procedures generally known in the art.

The said process further optionally comprising asymmetric reaction using chiral auxiliaries based synthesis (using carbohydrate, chiral amine or cyclic ketimine) and/or catalytic asymmetric Strecker synthesis (using guanidine, chiral Schiff base or BINOL-based catalyst).

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (1) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable salts and stereoisomeric forms thereof possess P2X7 receptor antagonizing properties as demonstrated in the Pharmacological Examples. Other examples of art-known group transformation reactions to convert compounds of formula (I) into other compounds of formula (I) are hydrolysis of carboxylic esters to the corresponding carboxylic acid or alcohol; hydrolysis of amides to the corresponding carboxylic acids or amines; alcohols may be converted into esters and ethers; primary amines may be converted into secondary or tertiary amines; double bonds may be hydrogenated to the corresponding single bond. The starting materials and some of the intermediates are known compounds and are commercially available or may be prepared according to conventional reaction procedures generally known in the art. The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example,by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials. In the preparation of the compounds of formula I and the starting materials and/or intermediates described herein it may be useful to protect certain groups which are sensitive to the reaction conditions. The evaluation of the usefulness of the optional protection, as well as the selection of the suitable protecting agent, according to the reaction carried out in the preparation of the compounds of the invention and the functional group to be protected, are within the common knowledge of the skilled person. The removal of the optional protective groups is carried out according to conventional techniques. For a general reference to the use of protective groups in orgamic chemistry, see Theodora W. Greene and Peter G. M. Wuts "Protective groups in organic synthesis", John Wiley & Sons, Inc., II Ed., 1991.

The preparation of the salts of the compounds of formula I is carried out according to known methods. Therefore the present compounds of formula (I) are useful as a medicine especially in the treatment of a condition or disease mediated by the P2X7 receptor, in particular P2X7 receptor antagonistic activity. Subsequently the present compounds may be used for the manufacture of a medicine for treatment of a condition or a disease mediated by P2X7 receptor activity, in particular P2X7 receptor antagonistic activity.

The present invention also provides the use of a compound of formula (I) or a pharmaceutically acceptable salt thereof for the manufacture of a medicament for the treatment of conditions or diseases selected from P2X7 receptor mediated conditions or diseases. In an embodiment, the present invention provides a compound of formula (I) for use as a medicine or for use in the treatment of conditions or diseases selected from P2X7 receptor mediated conditions or diseases. Further, the present invention also provides a method of treatment of a condition mediated by P2X7 receptor activity, in a mammalian subject, which method comprises administering to a mammal in need of such treatment a therapeutically effective amount of a compound of formula (I) or a pharmaceutically acceptable salt thereof. In view of the above described mechanisms of action, the compounds of the invention are useful for the treatment of neurodegenerative disorders of various origins such as Alzheimer's Disease and other dementia conditions such as Lewys body, fronto-temporal dementia and taupathies; amyotrophic lateral sclerosis, Multiple Sclerosis, Parkinson's Disease and other parkinsonian syndromes; HIV-induced neuroinflammation; essential tremors; other spino cerebellar degenerations and Charcot-Marie-Toot neuropathy. The compounds of the invention are also useful for the treatment of neurological conditions such as epilepsy including simple partial seizure, complex partial seizure, secondary generalized seizure, further including absence seizure, myoclonic seizure, clonic seizure, tonic seizure, tonic clonic seizure and atonic seizure.

The compounds of the invention are also useful for the treatment of cognitive disorders and of psychiatric disorders. Psychiatric disorders include, and are not limited to major depression, dysthymia, mania, bipolar disorder (such as bipolar disorder type I, bipolar disorder type II), cyclothymic disorder, rapid cycling, ultradian cycling, mania, hypomania, schizophrenia, schizophreniform disorders, schizoaffective disorders, personality disorders, attention disorders with or without hyperactive behaviour, delusional disorders, brief psychotic disorders, shared psychotic disorders, psychotic disorder due to a general medical condition, substance-induced psychotic disorders or a psychotic disorder not otherwise specified, anxiety disorders such as generalised anxiety disorder, panic disorders, post-traumatic stress disorder, impulse control disorders, phobic disorders, dissociative states and moreover in smoke, drug addiction and alcoholism. In particular bipolar disorders, psychosis, anxiety and addiction.

Tthe compounds of the present invention are useful in the prevention or treatment of neuropathic pain. Neuropathic pain syndromes include, and are not limited to: diabetic neuropathy; sciatica; non-specific lower back pain; multiple sclerosis pain; fibromyalgia; HIV-related neuropathy; neuralgia, such as post-herpetic neuralgia and trigeminal neuralgia, Morton's neuralgia, causalgia; and pain resulting from physical trauma, amputation, phantom limb, cancer, toxins or chronic inflammatory conditions; central pain such as the one observed in thalamic syndromes, mixed central and peripheral forms of pain such as complex regional pain syndromes (CRPS) also called reflex sympathetic dystrophies.

The compounds of the invention are also useful for the treatment of chronic pain. Chronic pain includes, and is not limited to, chronic pain caused by inflammation or an inflammatory-related condition, ostheoarthritis, rheumatoid arthritis, acute injury or trauma, upper back pain or lower back pain (resulting from systematic, regional or primary spine disease such as radiculopathy), bone pain (due to osteoarthritis, osteoporosis, bone metastasis or unknown reasons), pelvic pain, spinal cord injury-associated pain, cardiac chest pain, non-cardiac chest pain, central post-stroke pain, myofascial pain, sickle cell pain, cancer pain, Fabry's disease, AIDS pain, geriatric pain or pain caused by headache, temporomandibular joint syndrome, gout, fibrosis or thoracic outlet syndromes, in particular rheumatoid arthritis and osteoarthritis.

The compounds of the invention are also useful in the treatment of acute pain caused by acute injury, illness, sport-medicine injuries, carpal tunnel syndrome, burns, musculoskeletal sprains and strains, musculotendinous strain, cervicobrachial pain syndromes, dyspepsis, gastric ulcer, duodenal ulcer, dysmenorrhea, endometriosis or surgery (such as open heart or bypass surgery), post operative pain, kidney stone pain, gallbladder pain, gallstone pain, obstetric pain or dental pain.

The compounds of the invention are also useful in the treatment of headaches such as migraine, tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

Compounds of the invention are also useful in the treatment of diseases such as vertigo, tinnitus, muscle spasm, and other disorders including and not limited to cardiovascular diseases (such as cardiac arrhythmia, cardiac infarction or angina pectoris, hypertension, cardiac ischemia, cerebral ischemia) endocrine disorders (such as acromegaly or diabetes insipidus) diseases in which the pathophysiology of the disorder involves excessive or hypersecretory or otherwise inappropriate cellular secretion of an endogenous substance (such as catecholamine, a hormone or a growth factor).

The compounds of the invention are also useful in the selective treatment of liver disease, such as inflammatory liver diseases, for example chronic viral hepatitis B, chronic viral hepatitis C, alcoholic liver injury, primary biliary cirrhosis, autoimmune hepatitis, liver fibrosis, non-alcoholic steatohepatitis and liver transplant rejection.

The compounds of the invention inhibit inflammatory processes affecting all body systems. Therefore are useful in the treatment of inflammatory processes of the muscular-skeletal system of which the following is a list of examples but it is not comprehensive of all target disorders: arthritic conditions such as alkylosing spondylitis, cervical arthritis, fibromyalgia, gout, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: periarthritis nodosa, thyroiditis, aplastic anaemia, scleroderma, myasthenia gravis, multiple sclerosis and other demyelinizating disorders, encephalomyelitis, sarcoidosis, nephritic syndrome, Bechet's syndrome, polymyositis, gingivitis.

Compounds of the invention are also useful in the treatment of gastrointestinal (GI) tract disorders such as inflammatory bowel disorders including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varialoforme, ulcerative colitis, peptic ulceration, pyrosis, and other damage to the GI tract, for example, by *Helicobacter pylori*, gastroesophageal reflux disease, gastroparesis, such as diabetic gastroparesis; and other functional bowel disorders, such as non-ulcerative dyspepsia (NUD); emesis, diarrhoea, and visceral inflammation.

Compounds of the invention are also useful in the treatment of disorders of the genito-urinary tract such as overactive bladder, prostatitis (chronic bacterial and chronic non-bacterial prostatitis), prostadynia, interstitial cystitis, urinary incontinence and benign prostatic hyperplasia, annexities, pelvic inflammation, bartholinities and vaginitis. In particular, overactive bladder and urinary incontinence.

The compounds of the invention are also useful in the treatment of ophthalmic diseases such as retinitis, retinopathies, uveitis and acute injury to the eye tissue, age-related macular degeneration or glaucoma, conjunctivitis.

The compounds of the invention are also useful in the treatment of eating disorders such as anorexia nervosa including the subtypes restricting type and binge-eating/purging type; bulimia nervosa including the subtypes purging type and non-purging type; obesity; compulsive eating disorders; binge eating disorder; and eating disorder not otherwise specified.

The compounds of the invention are also useful in the treatment of allergie dermatitis, hyperresponsiveness of the airway, chronic obstructive pulmonary disease (COPD), bronchitis, septic shock, Sjogren's syndrome, glomerulonephritis, atherosclerosis, growth and metastases of malignant cells, myoblastic leukaemia, diabetes, meningitis, osteoporosis, burn injury, ischaemic heart disease, stroke, peripheral vascular disease, varicose veins, glaucoma.

The term "treating" and "treatment", as used herein, refers to curative, palliative and prophylactic treatment, including reversing, alleviating, inhibiting the progress of, or preventing the disease, disorder or condition to which such term applies, or one or more symptoms of such disease, disorder or condition.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oralliquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient.

Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (1), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage.

"Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1', 6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume). The pharmaceutically acceptable flavours which can mask the bitter tasting ingredients in the low-dosage formulations comprise preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like.

Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of diseases linked to the mediation of the ligand-gated ion channels will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

As used herein, a "therapeutically effective amount" of a compound, is the quantity of a compound which, when administered to an individual or animal, results in a sufficiently high level of that compound in the individual or animal to cause a discernible P2X7 receptor antagonistic response.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

Nomenclature and Structures

In general, the nomenclature used in this Application is based on ChemSketch™ (ACDLabs) and generated according to the IUPAC systematic nomenclature. Chemical structures shown herein were prepared using ISIS® version 2.2. Any open valency appearing on a carbon, oxygen, sulfur, or nitrogen atom in the structures herein indicates the presence of a hydrogen atom unless indicated otherwise. Where a nitrogen-containing heteroaryl ring is shown with an open valency on a nitrogen atom and variables such as $R^1$, $R^2$, $R^3$ etc. are shown on the heteroaryl ring, such variables may be bound or joined to the open valency nitrogen. Where a chiral center exists in a structure but no specific stereochemistry is shown for the chiral center, both enentiomers associated with the chiral center are encompassed by the structure. Where a structure shown herein may exist in multiple tautomeric forms, all such tautomers are encompassed by the structure. The atoms represented in the structure herein are intended to encompass all naturally occurring isotopes of such atoms. Thus, for example, the hydrogen atoms represented herein are meant to include deuterium and tritium, and the carbon atoms are meant to include $^{13}C$ and $^{14}C$ isotopes.

Abbreviations

Abbreviations which may be used in the description of the Schemes and the Examples that follows are:
AcOH: Acetic acid
Anh: Anhydrous
AcONa: Sodium acetate
Boc: Tert-butyl-carbonate
Boc$_2$O: Di-tert-butyl dicarbonate
CC: Column Chromatography
DAST: Diethylaminosulfur trifluoride
DCM: Dichloromethane
DEA: Diethylamine
DIAD: Diisopropylazodicarboxylate
DIBAL: Diisobutylaluminiumhydride
DIPEA: Diisopropylethylenamine
DMAP: Dimethylaminopyridine
DMF: Dimethylformamide
DMSO: Dimethylsulfoxide
Et$_2$O: Diethyl ether
EtOAc: Ethyl acetate
EtOH: Ethanol
ESI: Electrospray ionization
HBTU: N,N,N',N'-Tetramethyl-O-(1H-benzotriazol-1-yl)uronium hexafluorophosphate;
h: hour;
Hrs: hours
M: Molar
MeCN: Acetonitrile
MeOH: Methanol
Min: Minute(s)
Ni-Raney: Nickel-Raney
NMR: Nuclear Magnetic Resonance
rt: Room Temperature
TFA Trifluoroacetic acid
THF: Tetrahydrofurane;
TLC: Thin Layer Chromatography
TMSCN Trimethylsilylcyanide;
UPLC-MS: UltraPerformance LiquidChromatography-Mass Spectrometry
XPhos: 4,5-bis(diphenylphosphino)-9,9-dimethylxantene.

Experimental Part

The following examples illustrate the present invention. Unless explicitly stated otherwise, all particulars (especially percentages and amounts) relate to the weight.

Synthetic Examples

A. Synthesis of the Intermediates 1b-1d a) Preparation of

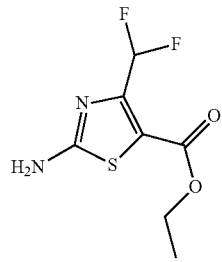

Intermediate (1b)

Sulfuryl chloride (1.23 mL, 15.2 mmol, 1.01 eq) was added dropwise at 0° C. to ethyl 4,4-difluoroacetoacetate (2.5 g, 15.0 mmol, 1 eq) under nitrogen atmosphere, and stirred overnight at room temperature. The reaction was diluted with EtOAc (20 mL) and poured into an ice/water mixture (20 mL). The organic layer was dried over anh. Na$_2$SO$_4$, filtered and evaporated giving 3.2 g of crude in 2-chloro-4,4-difluoroacetoacetate as a yellow oil. The crude was dissolved in ethanol (10 mL), treated with thiourea (3.2 g, 30 mmol, 2 eq) and heated in a microwave reactor for 1 h at 100° C. Then, the solvent was removed in vacuo and the residue partitioned in sat. NaHCO$_3$ (10 mL) and EtOAc (10 mL). The organic layer was washed with brine (20 mL), dried over anh. Na$_2$SO$_4$, filtered and evaporated. The crude was treated with diethyl ether, filtered and dried in vacuo, giving 1.37 g (yield 41%) of intermediate 1b as a yellow solid.

b) Preparation of

Intermediate (1c)

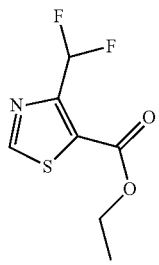

Intermediate 1b (1.37 g, 6.16 mmol, 1 eq) was dissolved in dioxane (35 mL), isoamylnitrite (2.24 mL, 16.64 mmol, 2.7 eq) was added and the reaction mixture was heated for 1 hour at 80° C. Solvent was removed by evaporation under reduced pressure, and the residue was purified by flash chromatography over silica gel (EtOAc/petroleum ether 10/90) yielding intermediate 1c (1.02 g, yield 80%) as a yellow solid.

c) Preparation of

Intermediate (1d)

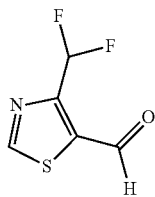

Intermediate 1c (0.758 g, 3.66 mmol, 1 eq) was dissolved in dry DCM (18.5 mL) under argon atmosphere and cooled to −75° C. 1M diisobutyl aluminium hydride in DCM (4.1 mL, 4.1 mmol, 1.12 eq) was added dropwise and the reaction mixture was stirred at −70° C. After 1.5 h, 1M diisobutyl aluminium hydride in DCM (2.5 mL, 2.5 mmol, 0.6 8eq) was added dropwise and the reaction mixture was stirred additionally for 1 h at −70°. The reaction was warmed to 0° C. and treated with water (0.264 mL), 15% NaOH (0.264 mL) and water (0.66 mL) in this order. It was then stirred for 5 minutes at 0° C., then for 30 minutes at room temperature. Water (0.24 mL) followed by 15% NaOH (0.130 mL) were sequentially added, and the reaction was stirred at room temperature until a precipitate was formed. The mixture was filtered and then the solvent was concentrated. The residue was purified by flash chromatography over silica gel (DCM/petroleum ether 80/20-100% DCM) yielding a yellow oil (0.34 mg, yield 40%) containing intermediate 1d (purity ≈70%), that was used as such.

B. Synthetis of Intermediates: α-Aminonitriles
Starting Materials

All substituted 4-phenyloxy or 4-benzyloxy piperidine derivatives and 4-methyl-1,3-thiazole-5-carbaldehyde, used as starting materials, were purchased from chemical providers:

| Structures of starting materials | CAS |
|---|---|
| | 81151-35-1 |
| | 86810-95-9 |
| | 1185298-16-1 |
| | n.a. |
| | 1121595-12-7 |
| | n.a. |
| | 3413-28-3 |
| | 63843-53-8 |
| | 3202-36-6 |
| | 3413-29-4 |

-continued

| Structures of starting materials | CAS |
|---|---|
| 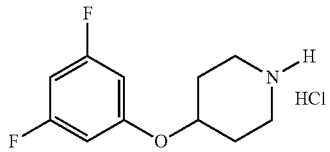 [SMILES: Fc1cc(F)cc(OC2CCNCC2)c1 ; Cl] | n.a |
| 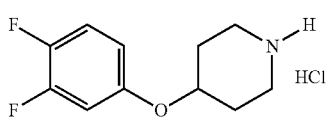 [SMILES: Fc1ccc(OC2CCNCC2)cc1F ; Cl] | 204013-09-2 |
| 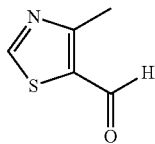 | 82294-70-0 |
| 2-Chloro-6-fluorobenzoic acid | 434-75-3 |
| Quinoline-5-carboxylic acid | 7250-53-5 |

General Procedure

A hydrochloride of 4-substituted piperidine derivative (1 eq) was suspended in 2-3 mL of DCM and TEA (1.1-2 eq) was added. Mixture was stirred for several minutes, solvent were evaporated on rotatory evaporator and residue was vacuum dried for 15 minutes at 40° C. Hydrochloride-free amine (1 eq), thiazolyl-aldehyde (180-300 mg, 1.2-1.5 eq), and AcONa (3.5 eq) were dissolved in glacial AcOH (5-8 mL). The mixture was stirred at room temperature under Argon for 3 h and then cooled to 0° C. TMSCN (3-12 eq) was added dropwise and the mixture was allowed to warm to room temperature and stirred for 1-3 days. In the meanwhile, if necessary according to LC-MS analysis, TMSCN (3-6 eq) was added (up to 12 eq of TMSCN) and reaction was stirred for 24 h. Then the solvent was evaporated on a rotatory evaporator at 40-45° C. A saturated solution of NaHCO$_3$ (20-50 mL) was added to the residue. If necessary, solid NaHCO$_3$ and water was added for increase pH to 8. The mixture was extracted with DCM (5 mL×3-5). The combined organic phases were dried (anh. Na$_2$SO$_4$) and evaporated. The crude was purified by flash chromatography (SiO$_2$) with hexane/acetone mixture (0->30%) giving the pure α-aminonitrile (28-68% yield).

Using this procedure, intermediates A0018_42_01 (yield 54%), A0018_42_02 (yield 55%), A0018_42_03 (yield 55%), A0018_42_04 (yield 42%), A0018_42_05 (yield 63%), A0018_42_06 (yield 50%), A0018_41_01 (yield 45%), A0018_41_02 (yield 60%), A0018_41_03 (yield 46%), A0018_41_04 (yield 68%), A0018_41_05 (yield 65%), A0018_41_06 (yield 43%), A00FF_42_04 (yield 30%), A00FF_42_05 (yield 56%), A00FF_42_06 (yield 36%), A00FF_41_01 (yield 31%), A00FF_41_02 (yield 57%), A00FF_41_03 (yield 53%), A00FF_41_04 (yield 53%), A00FF_41_05 (yield 28%) were prepared starting from 4-methyl-1,3-thiazole-5-carbaldehyde or, respectively, 4-difluoromethyl-1,3-thiazole-5-carbaldehyde and 4-(4-fluorobenzyloxypiperidine), 4-(4-chlorobenzyloxypiperidine), 4-(3-fluorobenzyloxypiperidine), 4-(2-fluorobenzyloxypiperidine), 4-(3,5-difluorobenzyloxypiperidine), 4-(3,4-difluorobenzyloxypiperidine), 4-(4-fluorophenyloxypiperidine), 4-(4-chlorophenyloxypiperidine), 4-(3-fluorophenyloxypiperidine), 4-(2-fluorophenyloxypiperidine), 4-(3,5-difluorophenyloxypiperidine) or 4-(3,4-difluorophenyloxypiperidine).

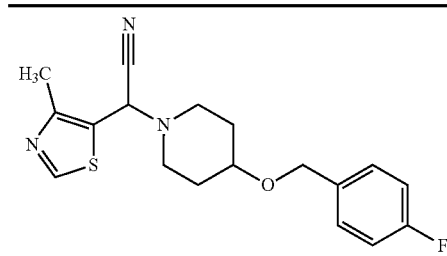

A0018_42_01

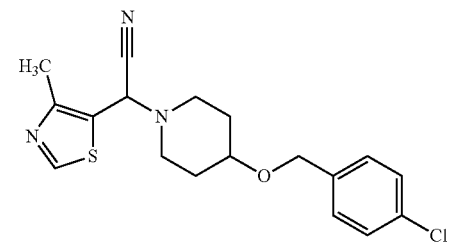 [SMILES: Cc1ncsc1C(C#N)N1CCC(OCc2ccc(Cl)cc2)CC1]

A0018_42_02

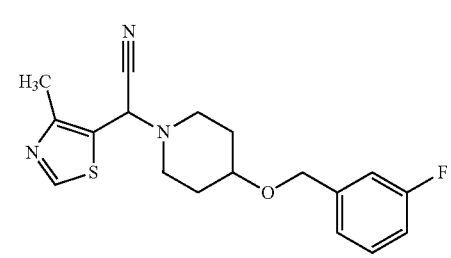 [SMILES: Cc1ncsc1C(C#N)N1CCC(OCc2cccc(F)c2)CC1]

A0018_42_03

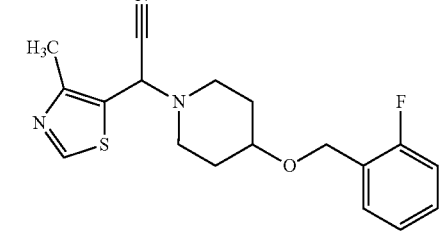

A0018_42_04

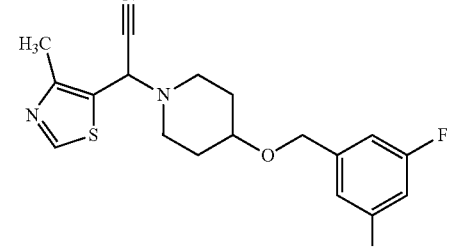

A0018_42_05

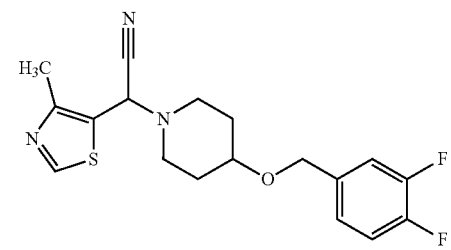 [SMILES: Cc1ncsc1C(C#N)N1CCC(OCc2ccc(F)c(F)c2)CC1]

A0018_42_06

-continued
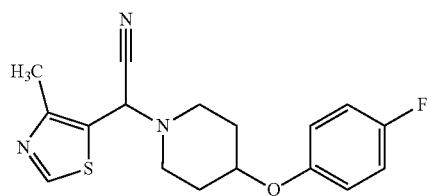 [SMILES: Cc1ncsc1C(C#N)N1CCC(Oc2ccc(F)cc2)CC1] A0018_41_01
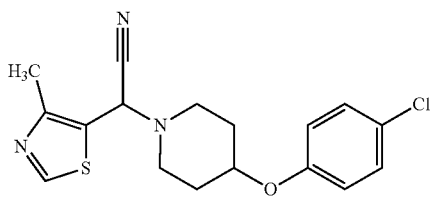 [SMILES: Cc1ncsc1C(C#N)N1CCC(Oc2ccc(Cl)cc2)CC1] A0018_41_02
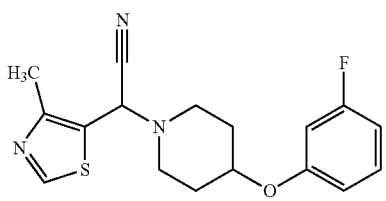 [SMILES: Cc1ncsc1C(C#N)N1CCC(Oc2cccc(F)c2)CC1] A0018_41_03
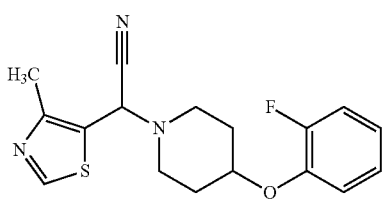 [SMILES: Cc1ncsc1C(C#N)N1CCC(Oc2ccccc2F)CC1] A0018_41_04
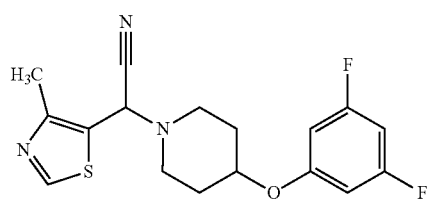 [SMILES: Cc1ncsc1C(C#N)N1CCC(Oc2cc(F)cc(F)c2)CC1] A0018_41_05
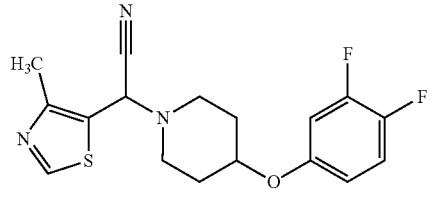 [SMILES: Cc1ncsc1C(C#N)N1CCC(Oc2ccc(F)c(F)c2)CC1] A0018_41_06
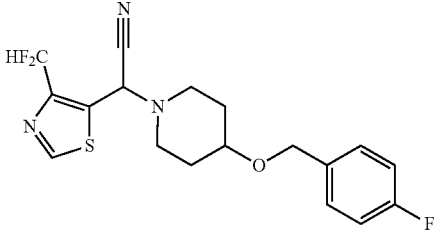 [SMILES: N#CC(c1scnc1C(F)F)N1CCC(OCc2ccc(F)cc2)CC1] A00FF_42_01
-continued
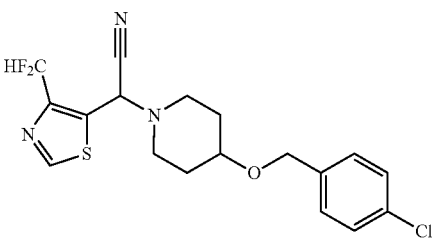 [SMILES: N#CC(c1scnc1C(F)F)N1CCC(OCc2ccc(Cl)cc2)CC1] A00FF_42_02
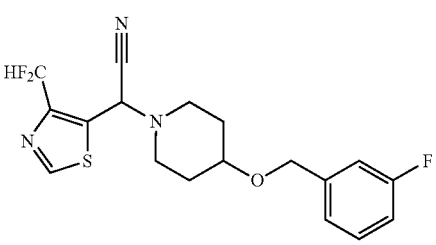 [SMILES: N#CC(c1scnc1C(F)F)N1CCC(OCc2cccc(F)c2)CC1] A00FF_42_03
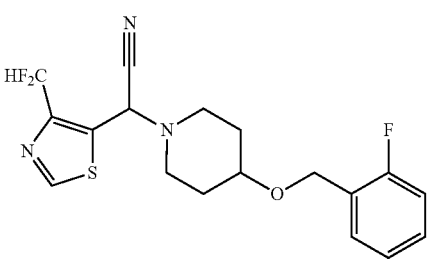 [SMILES: N#CC(c1scnc1C(F)F)N1CCC(OCc2ccccc2F)CC1] A00FF_42_04
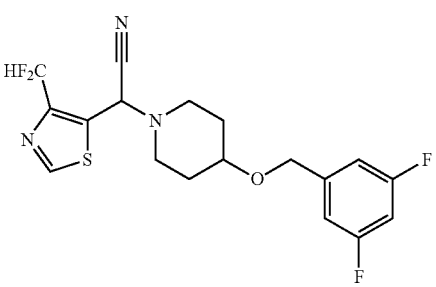 [SMILES: N#CC(c1scnc1C(F)F)N1CCC(OCc2cc(F)cc(F)c2)CC1] A00FF_42_05
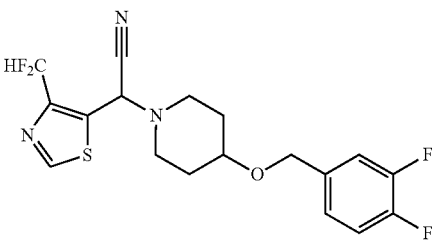 [SMILES: N#CC(c1scnc1C(F)F)N1CCC(OCc2ccc(F)c(F)c2)CC1] A00FF_42_06
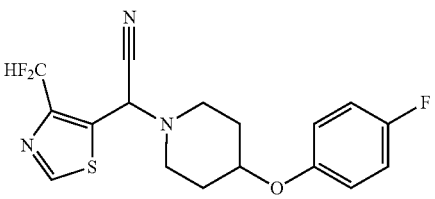 [SMILES: N#CC(c1scnc1C(F)F)N1CCC(Oc2ccc(F)cc2)CC1] A00FF_41_01

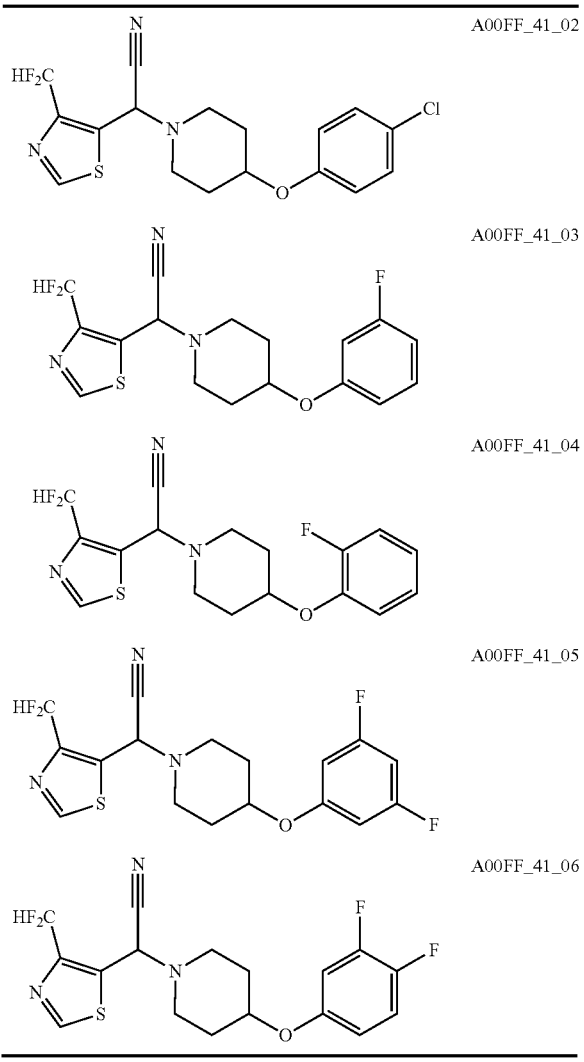

C. Preparation of Diamines (General Procedure)

A cyanide derivative (100-270 mg, 1 eq) was dissolved in dry DCM under Argon atmosphere and cooled in an ice-salt bath. A 1M solution of DIBAL (3 eq) in DCM was slowly added (portionwise, 1 eq every 30 minutes) and the mixture was stirred for an additional hour. To this solution (at 0° C.), water (1 ml) was added dropwise and the mixture was stirred until formation of precipitate was completed. DCM was removed in vacuum and the residue was suspended in AcOEt. The obtained solid was filtered and washed 4-6 times with AcOEt. Combined organic layers were dried over $Na_2SO_4$, evaporated to yield an oily residue and dried no shorter than 1 h in vacuum at 38-40° C. The crude product (68-97% yield) was used without additional purification in the next synthetic step.

Using this procedure:

intermediate A0017_59_01 (yield 94%) was prepared starting from A001842_01;

intermediate A0017_59_02 (yield 83%) was prepared starting from A001842_02;

intermediate A0017_59_03 (yield 87%) was prepared starting from A0018_4203;

intermediate A0017_59_04 (yield 97%) was prepared starting from A001842_04;

intermediate A0017_59_05 (yield 65%) was prepared starting from A001842_05;

intermediate A0017_59_06 (yield 88%) was prepared starting from A001842_06;

intermediate A0017_58_01 (yield 62%) was prepared starting from A0018_41_01;

intermediate A0017_58_02 (yield 95%) was prepared starting from A0018_41_02;

intermediate A0017_58_03 (yield 67%) was prepared starting from A0018_41_03;

intermediate A0017_58_04 (yield 89%) was prepared starting from A0018_41_04;

intermediate A0017_58_05 (yield 80%) was prepared starting from A0018_41_05;

intermediate A0017_58_06 (yield 95%) was prepared starting from A0018_41_06;

intermediate A00FF_59_04 (yield 87%) was prepared starting from A00FF_42_04;

intermediate A00FF 59_05 (yield 81%) was prepared starting from A00FF_42_05;

intermediate A00FF_59_06 (yield 80%) was prepared starting from A00FF_42_06;

intermediate A00FF_58_01 (yield 89%) was prepared starting from A00FF_41_01;

intermediate A00FF_58_02 (yield 94%) was prepared starting from A00FF_41_02;

intermediate A00FF_58_03 (yield 88%) was prepared starting from A00FF_41_03;

intermediate A00FF_58_04 (yield 92%) was prepared starting from A00FF_41_04 intermediate A00FF_58_05 (yield 93%) was prepared starting from A00FF_41_05.

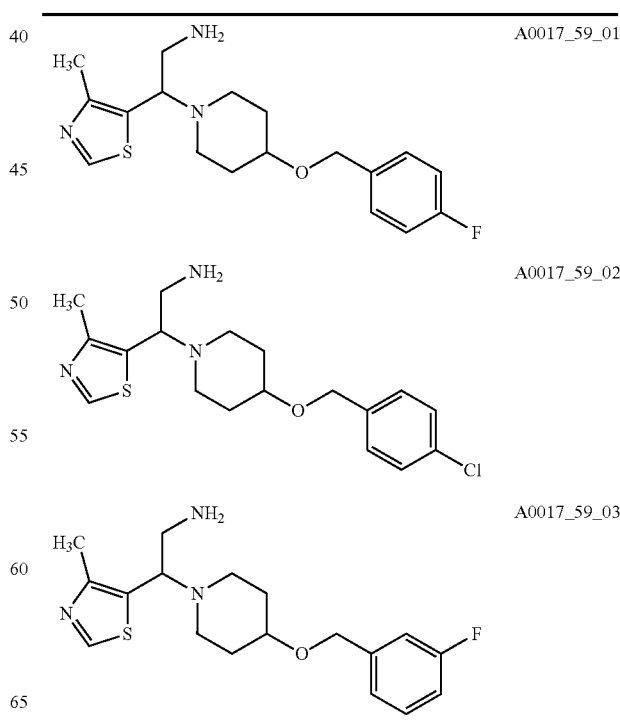

-continued
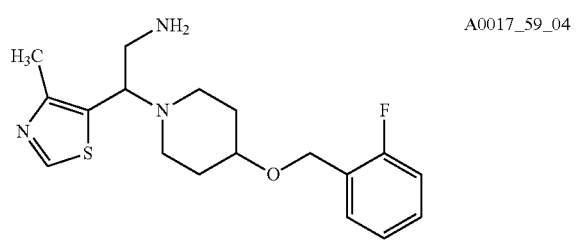
A0017_59_04
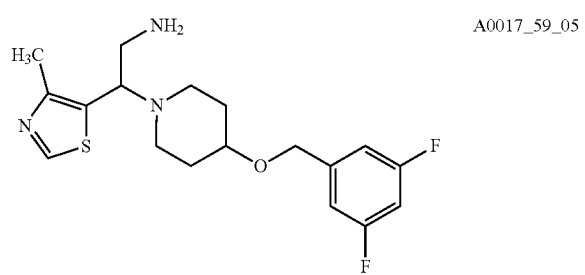
A0017_59_05
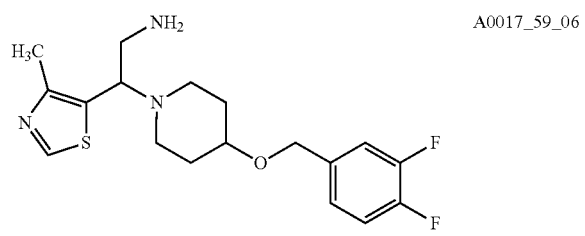
A0017_59_06
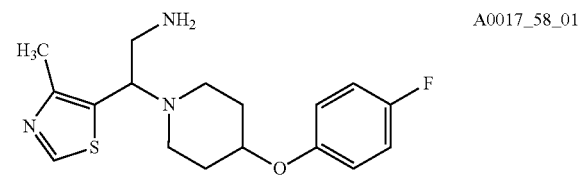
A0017_58_01
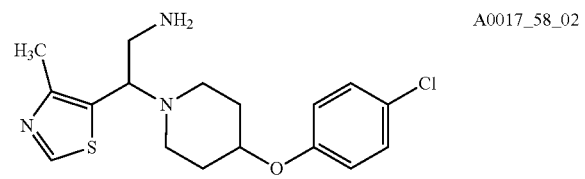
A0017_58_02
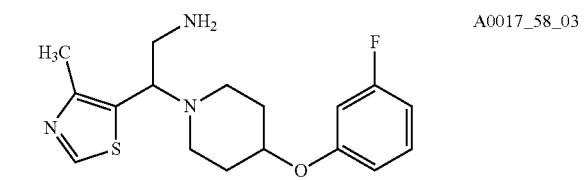
A0017_58_03
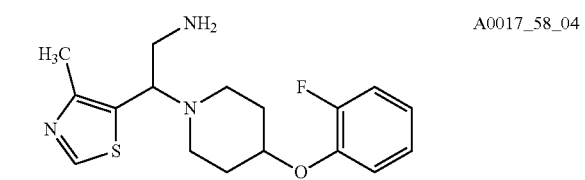
A0017_58_04
-continued
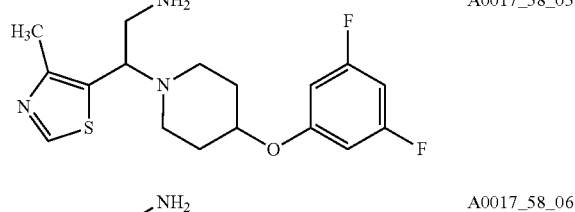
A0017_58_05
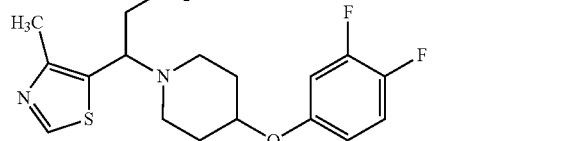
A0017_58_06
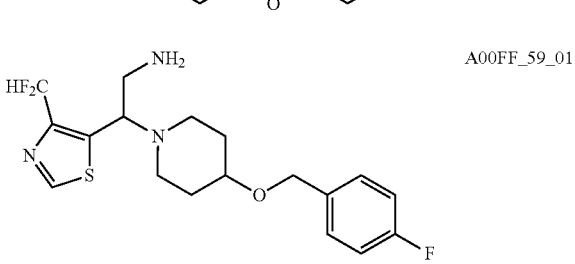
A00FF_59_01
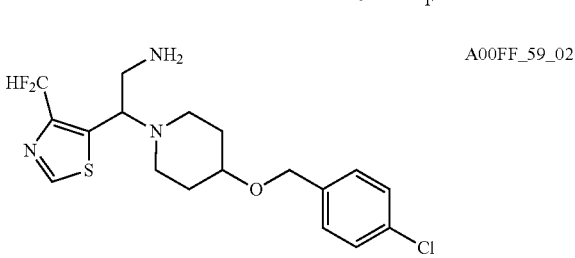
A00FF_59_02
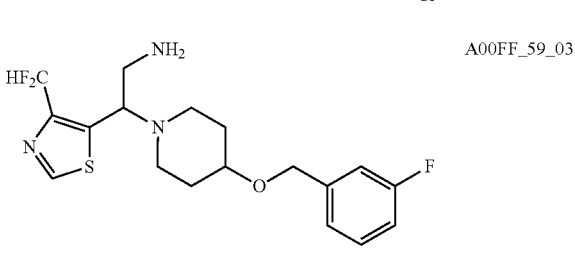
A00FF_59_03
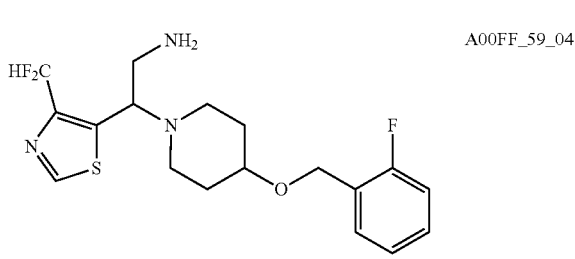
A00FF_59_04
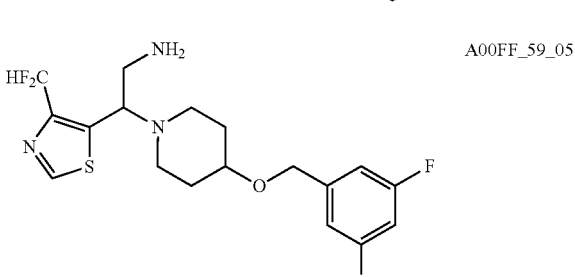
A00FF_59_05

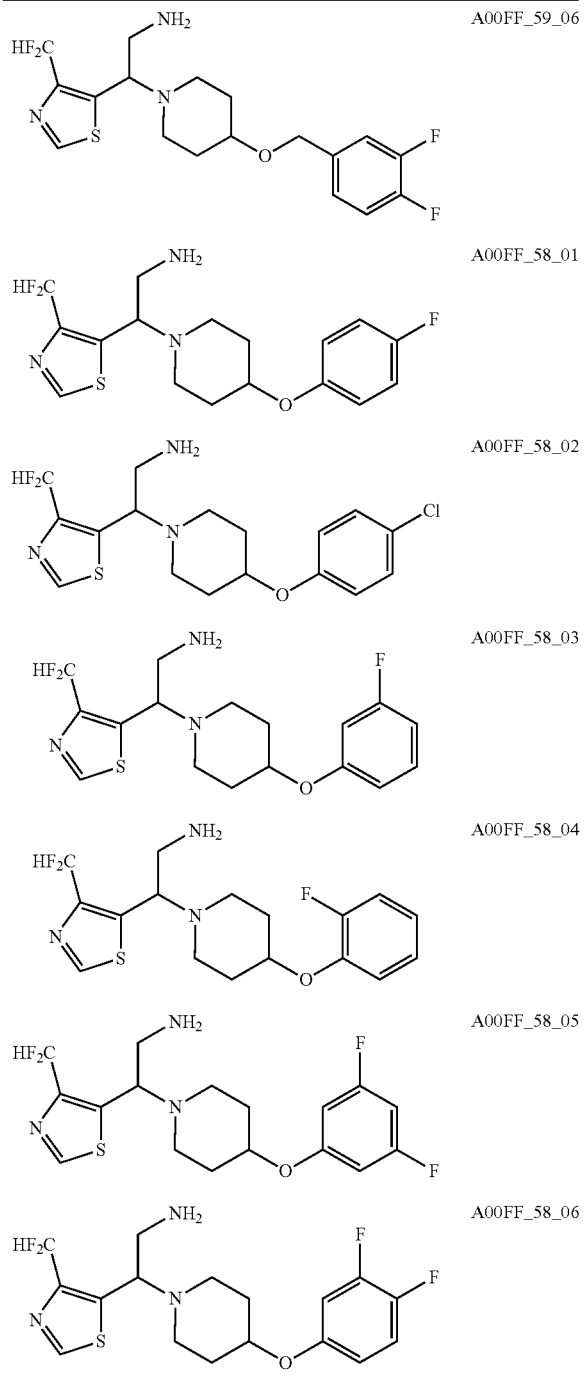

D. General Procedure for the Synthesis of Final Compounds

Preparation of Compounds 1-38

A mixture of carboxylic acid (25-115 mg, 1 eq), HATU (1,1 eq) or EDCl (1 eq)/HOBt (1 eq) and DIPEA (2-3 eq) in anhydrous DMF or DCM (1-2 mL) was stirred for 10-30 minutes under Argon atmosphere. Then, a solution of crude amine (1 eq) in anhydrous DCM or DMF (1-3 mL) was added and the reaction mixture was stirred overnight. Water and saturated $NaHCO_3$ were added and the product was extracted 4-6 times with DCM. Combined organic layers were dried over $Na_2SO_4$ and evaporated. Product was purified via FCC ($SiO_2$, DCM->AcOEt->0-10 MeOH/AcOEt) or SFC (5-10% MeOH/$scCO_2$) and the fractions with desired product were evaporated and dried under high vacuum for 16-72 h. Yields 8-71%.

Using this procedure compounds:

Compound 1 (yield 19%) was prepared starting from 2-chloro-6-fluorobenzoic acid, HATU and A0017_59_01 in DMF+DCM, purification by SFC;

Compound 2 (yield 19%) was prepared starting from 2-chloro-6-fluorobenzoic acid, HATU and A0017_59_02 in DMF, purification by SFC;

Compound 3 (yield 23%) was prepared starting from 2-chloro-6-fluorobenzoic acid, EDCl/HOBt and A0017_59_03 in DCM, purification by SFC;

Compound 4 (yield 30%) was prepared starting from 2-chloro-6-fluorobenzoic acid, HATU and A0017_59_04 in DMF, purification by SFC;

Compound 5 (yield 16%) was prepared starting from 2-chloro-6-fluorobenzoic acid, HATU and A0017_59_05 in DMF, purification by FCC followed by SFC;

Compound 6 (yield 12-18%) was prepared starting from 2-chloro-6-fluorobenzoic acid, EDCl/HOBt or HATU and A0017_59_06 in DCM or DMF+DCM, purification by SFC;

Compound 7 (yield 16%) was prepared starting from 2-chloro-6-fluorobenzoic acid, HATU and A0017_58_01 in DMF+DCM, purification by SFC;

Compound 8 (yield 13-16%) was prepared starting from 2-chloro-6-fluorobenzoic acid, HATU and A0017_58_02 in DMF+DCM or DMF, purification by FCC preceded by SFC;

Compound 9 (yield 48%) was prepared starting from 2-chloro-6-fluorobenzoic acid, HATU and A0017_58_03 in DMF, purification by FCC;

Compound 10 (yield 12%) was prepared starting from 2-chloro-6-fluorobenzoic acid, HATU and A0017_58_04 in DMF, purification by FCC;

Compound 11 (yield 8%) was prepared starting from 2-chloro-6-fluorobenzoic acid, HATU and A0017_58_05 in DCM, purification by SFC preceded by FCC;

Compound 12 (yield 29%) was prepared starting from 2-chloro-6-fluorobenzoic acid, HATU and A0017_58_06 in DMF+DCM, purification by SFC;

Compound 13 (yield 28%) was prepared starting from quinoline-5-carboxylic acid, HATU and A0017_59_01 in DCM, purification by FCC;

Compound 14 (yield 25%) was prepared starting from quinoline-5-carboxylic acid, HATU and A0017_59_02 in DMF, purification by FCC;

Compound 15 (yield 32%) was prepared starting from quinoline-5-carboxylic acid, HATU and A0017_59_03 in DMF+DCM, purification by FCC;

Compound 16 (yield 31%) was prepared starting from quinoline-5-carboxylic acid, HATU and A0017_59_04 in DMF+DCM, purification by FCC;

Compound 17 (yield 29%) was prepared starting from quinoline-5-carboxylic acid, HATU and A0017_59_05 in DMF, purification by FCC;

Compound 18 (yield 20%) was prepared starting from quinoline-5-carboxylic acid, EDCl/HOBt and A0017_59_06 in DCM, purification by FCC;

Compound 19 (yield 28%) was prepared starting from quinoline-5-carboxylic acid, HATU and A0017_58_01 in DMF, purification by FCC;

Compound 20 (yield 27%) was prepared starting from quinoline-5-carboxylic acid, HATU and A0017_58_02 in DMF, purification by FCC;

Compound 21 (yield 71%) was prepared starting from quinoline-5-carboxylic acid, HATU and A0017_58_03 in DMF, purification by FCC;

Compound 22 (yield 25%) was prepared starting from quinoline-5-carboxylic acid, HATU and A0017_58_04 in DMF, purification by FCC;

Compound 23 (yield 15%) was prepared starting from quinoline-5-carboxylic acid, EDCl/HOBt and A0017_58_05 in DCM, purification by FCC;

Compound 24 (yield 17-27%) was prepared starting from quinoline-5-carboxylic acid, EDCl/HOBt or HATU and A0017_58_06 in DCM or DMF+DCM, purification by FCC;

Compound 25 (yield 30%) was prepared starting from 2-chloro-6-fluorobenzoic acid, HATU and A00FF_59_04 in DMF+DCM, purification by SFC;

Compound 26 (yield 19%) was prepared starting from 2-chloro-6-fluorobenzoic acid, HATU and A00FF_59_05 in DMF+DCM, purification by two individual FCC;

Compound 27 (yield 26%) was prepared starting from 2-chloro-6-fluorobenzoic acid, HATU and A00FF_59_06 in DMF+DCM, purification by SFC;

Compound 28 (yield 19%) was prepared starting from 2-chloro-6-fluorobenzoic acid, HATU and A00FF_58_02 in DMF+DCM, purification by SFC;

Compound 29 (yield 22%) was prepared starting from 2-chloro-6-fluorobenzoic acid, HATU and A00FF_58_03 in DMF+DCM, purification by SFC;

Compound 30 (yield 30%) was prepared starting from 2-chloro-6-fluorobenzoic acid, HATU and A00FF_58_04 in DMF+DCM, purification by SFC;

Compound 31 (yield 29%) was prepared starting from 2-chloro-6-fluorobenzoic acid, HATU and A00FF_58_05 in DMF+DCM, purification by SFC;

Compound 32 (yield 30%) was prepared starting from quinoline-5-carboxylic acid, HATU and A00FF_59_04 in DMF+DCM, purification by SFC;

Compound 33 (yield 31%) was prepared starting from quinoline-5-carboxylic acid, HATU and A00FF_59_05 in DMF+DCM, purification by SFC;

Compound 34 (yield 34%) was prepared starting from quinoline-5-carboxylic acid, HATU and A00FF_58_01 in DMF+DCM, purification by SFC preceded by FCC;

Compound 35 (yield 19%) was prepared starting from quinoline-5-carboxylic acid, HATU and A00FF_58_02 in DMF+DCM, purification by FCC preceded by SFC;

Compound 36 (yield 22%) was prepared starting from quinoline-5-carboxylic acid, HATU and A00FF_58_03 in DMF+DCM, purification by SFC;

Compound 37 (yield 22%) was prepared starting from quinoline-5-carboxylic acid, HATU and A00FF_58_04 in DMF+DCM, purification by SFC Compound 38 (yield 35%) was prepared starting from quinoline-5-carboxylic acid, HATU and A00FF_58_05 in DMF+DCM, purifcation by SFC.

Table 1 lists final compounds that were prepared and tested according to the experimental procedure described for Example 1.

TABLE 1

| Compound | Structure | UPAC Name |
|---|---|---|
| 1 | 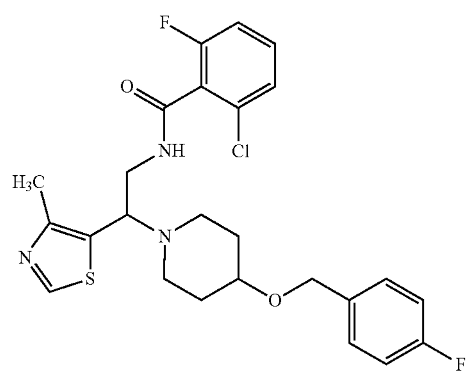 [SMILES: Cc1ncsc1C(CNC(=O)c1c(F)cccc1Cl)N1CCC(OCc2ccc(F)cc2)CC1] | 2-chloro-6-fluoro-N-(2-{4-[(4-fluorophenyl)methoxy]piperidin-1-yl)-2-(4-methyl-1,3-thiazol-5-yl}ethyl)benzamide |
| 2 | 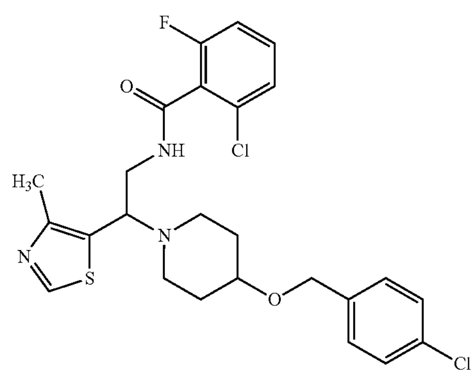 [SMILES: Cc1ncsc1C(CNC(=O)c1c(F)cccc1Cl)N1CCC(OCc2ccc(Cl)cc2)CC1] | 2-chloro-N-(2-{4-[(4-chlorophenyl)methoxy]piperidin-1-yl}-2-(4-methyl-1,3-thiazol-5-yl)ethyl)-6-fluorobenzamide |

TABLE 1-continued

| Compound | Structure | UPAC Name |
|---|---|---|
| 3 | 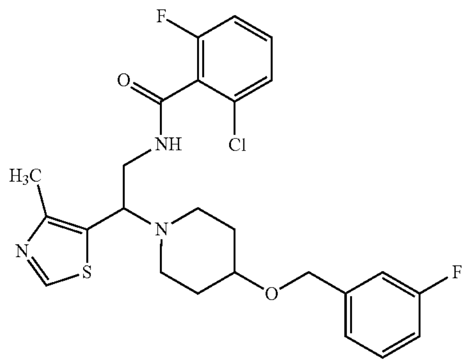 [SMILES: Cc1ncsc1C(CNC(=O)c1c(F)cccc1Cl)N1CCC(OCc2cccc(F)c2)CC1] | 2-chloro-6-fluoro-N-(2-{4-[(3-fluorophenyl)methoxy]piperidin-1-yl}-2-(4-methyl-1,3-thiazol-5-yl)ethyl)benzamide |
| 4 | 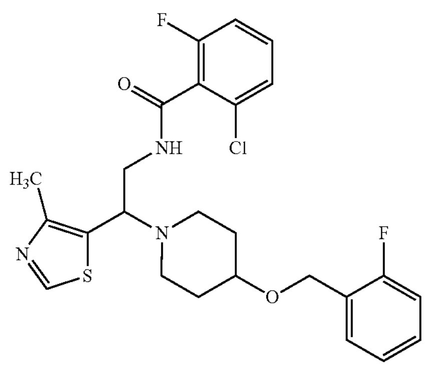 [SMILES: Cc1ncsc1C(CNC(=O)c1c(F)cccc1Cl)N1CCC(OCc2ccccc2F)CC1] | 2-chloro-6-fluoro-N-(2-{4-[(2-fluorophenyl)methoxy]piperidin-1-yl}-2-(4-methyl-1,3-thiazol-5-yl)ethyl)benzamide |
| 5 | 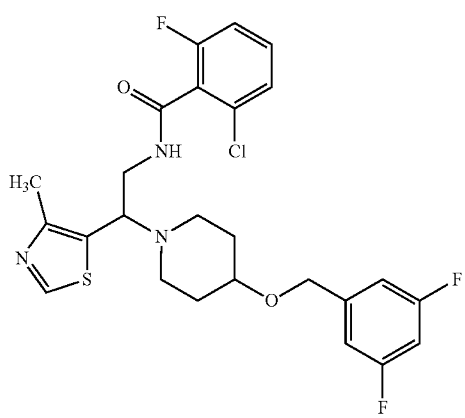 [SMILES: Cc1ncsc1C(CNC(=O)c1c(F)cccc1Cl)N1CCC(OCc2cc(F)cc(F)c2)CC1] | 2-chloro-N-(2-{4-[(3,5-difluorophenyl)methoxy]piperidin-1-yl}-2-(4-methyl-1,3-thiazol-5-yl)ethyl)-6-fluorobenzamide |
| 6 | 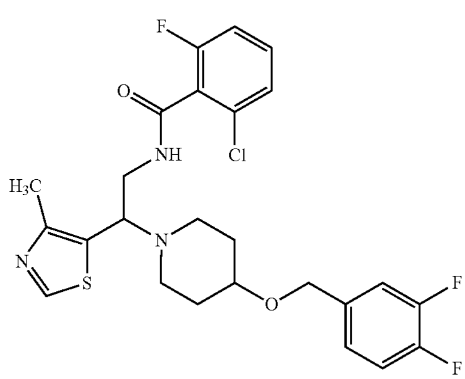 [SMILES: Cc1ncsc1C(CNC(=O)c1c(F)cccc1Cl)N1CCC(OCc2ccc(F)c(F)c2)CC1] | 2-chloro-N-(2-{4-[(3,4-difluorophenyl)methoxy]piperidin-1-yl}-2-(4-methyl-1,3-thiazol-5-yl)ethyl)-6-fluorobenzamide |

TABLE 1-continued

| Compound | Structure | UPAC Name |
|---|---|---|
| 7 | 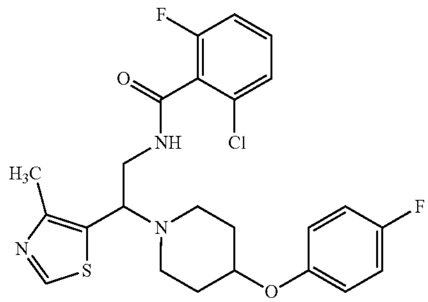 [SMILES: Cc1ncsc1C(CNC(=O)c1c(F)cccc1Cl)N1CCC(Oc2ccc(F)cc2)CC1] | 2-chloro-6-fluoro-N-{2-[4-(4-fluorophenoxy)piperidin-1-yl]-2-(4-methyl-1,3-thiazol-5-yl)ethyl}benzamide |
| 8 | 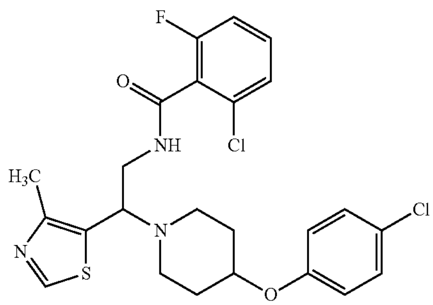 [SMILES: Cc1ncsc1C(CNC(=O)c1c(F)cccc1Cl)N1CCC(Oc2ccc(Cl)cc2)CC1] | 2-chloro-N-{2-[4-(4-chlorophenoxy)piperidin-1-yl]-2-(4-methyl-1,3-thiazol-5-yl)ethyl}-6-fluorobenzamide |
| 9 | 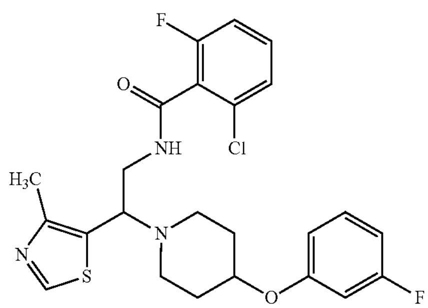 [SMILES: Cc1ncsc1C(CNC(=O)c1c(F)cccc1Cl)N1CCC(Oc2cccc(F)c2)CC1] | 2-chloro-6-fluoro-N-{2-[4-(3-fluorophenoxy)piperidin-1-yl]-2-(4-methyl-1,3-thiazol-5-yl)ethyl}benzamide |
| 10 | 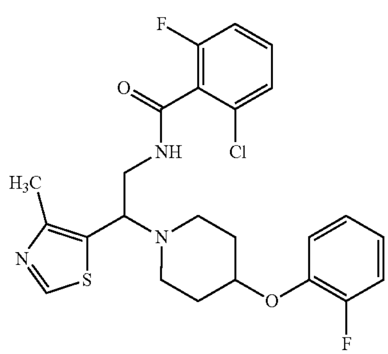 [SMILES: Cc1ncsc1C(CNC(=O)c1c(F)cccc1Cl)N1CCC(Oc2ccccc2F)CC1] | 2-chloro-6-fluoro-N-{2-[4-(2-fluorophenoxy)piperidin-1-yl]-2-(4-methyl-1,3-thiazol-5-yl)ethyl}benzamide |
| 11 | 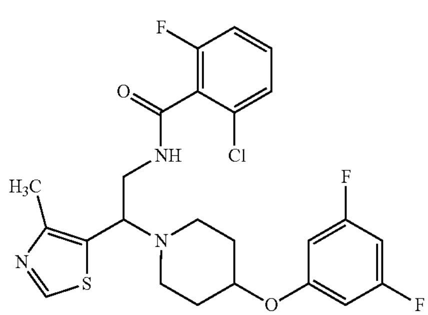 [SMILES: Cc1ncsc1C(CNC(=O)c1c(F)cccc1Cl)N1CCC(Oc2cc(F)cc(F)c2)CC1] | 2-chloro-N-{2-[4-(3,5-difluorophenoxy)piperidin-1-yl]-2-(4-methyl-1,3-thiazol-5-yl)ethyl}-6-fluorobenzamide |

TABLE 1-continued

| Compound | Structure | UPAC Name |
|---|---|---|
| 12 | 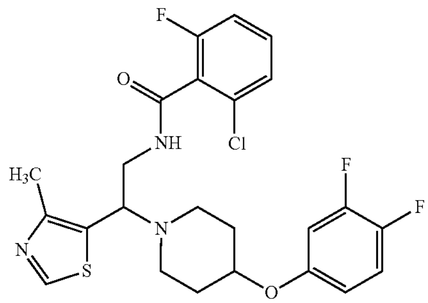 [SMILES: Cc1ncsc1C(CNC(=O)c1c(F)cccc1Cl)N1CCC(Oc2ccc(F)c(F)c2)CC1] | 2-chloro-N-{2-[4-(3,4-difluorophenoxy)piperidin-1-yl]-2-(4-methyl-1,3-thiazol-5-yl)ethyl}-6-fluorobenzamide |
| 13 | 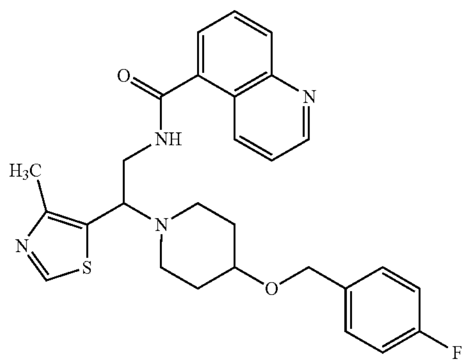 [SMILES: Cc1ncsc1C(CNC(=O)c1cccc2ncccc12)N1CCC(OCc2ccc(F)cc2)CC1] | N-(2-{4-[(4-fluorophenyl)methoxy]piperidin-1-yl}-2-(4-methyl-1,3-thiazol-5-yl)ethyl)quinoline-5-carboxamide |
| 14 | 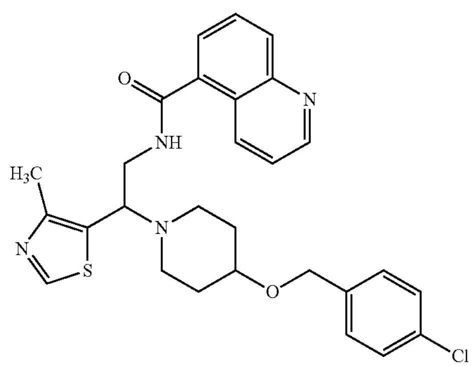 [SMILES: Cc1ncsc1C(CNC(=O)c1cccc2ncccc12)N1CCC(OCc2ccc(Cl)cc2)CC1] | N-(2-{4-[(4-chlorophenyl)methoxy]piperidin-1-yl}-2-(4-methyl-1,3-thiazol-5-yl)ethyl)quinoline-5-carboxamide |
| 15 | 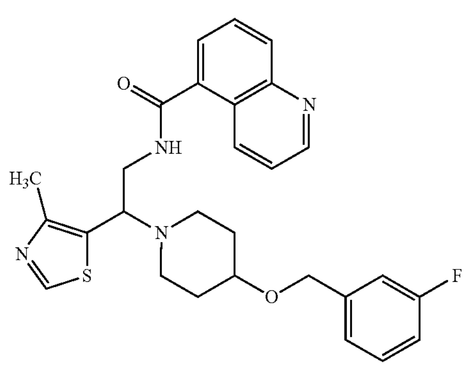 [SMILES: Cc1ncsc1C(CNC(=O)c1cccc2ncccc12)N1CCC(OCc2cccc(F)c2)CC1] | N-(2-{4-[(3-fluorophenyl)methoxy]piperidin-1-yl}-2-(4-methyl-1,3-thiazol-5-yl)ethyl)quinoline-5-carboxamide |

TABLE 1-continued

| Compound | Structure | UPAC Name |
|---|---|---|
| 16 | 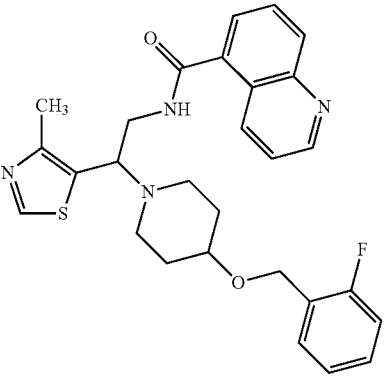 [SMILES: Cc1ncsc1C(CNC(=O)c1cccc2ncccc12)N1CCC(OCc2ccccc2F)CC1] | N-(2-{4-[(2-fluorophenyl)methoxy]piperidin-1-yl}-2-(4-methyl-1,3-thiazol-5-yl)ethyl)quinoline-5-carboxamide |
| 17 | 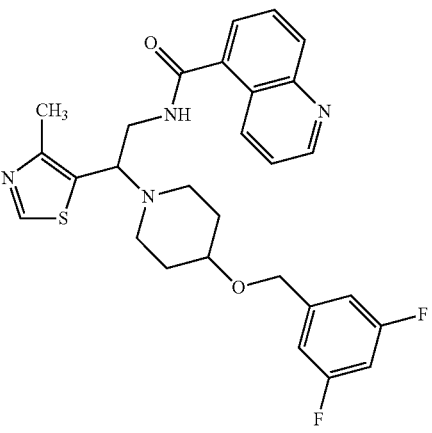 [SMILES: Cc1ncsc1C(CNC(=O)c1cccc2ncccc12)N1CCC(OCc2cc(F)cc(F)c2)CC1] | N-(2-{4-[(3,5-difluorophenyl)methoxy]piperidin-1-yl}-2-(4-methyl-1,3-thiazol-5-yl)ethyl)quinoline-5-carboxamide |
| 18 | 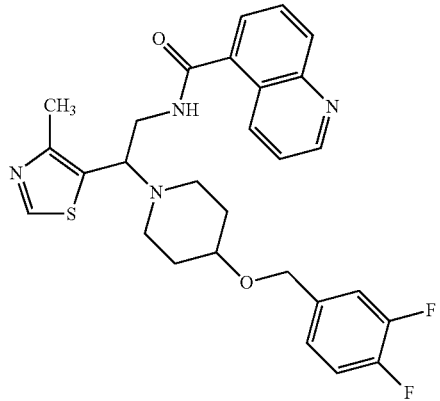 [SMILES: Cc1ncsc1C(CNC(=O)c1cccc2ncccc12)N1CCC(OCc2ccc(F)c(F)c2)CC1] | N-(2-{4-[(3,4-difluorophenyl)methoxy]piperidin-1-yl}-2-(4-methyl-1,3-thiazol-5-yl)ethyl)quinoline-5-carboxamide |
| 19 | 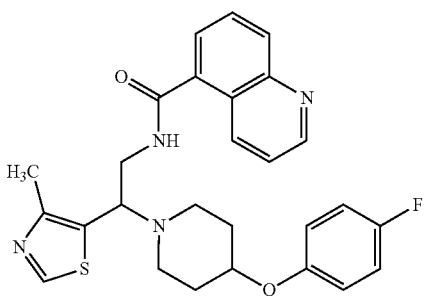 [SMILES: Cc1ncsc1C(CNC(=O)c1cccc2ncccc12)N1CCC(Oc2ccc(F)cc2)CC1] | N-{2-[4-(4-fluorophenoxy)piperidin-1-yl]-2-(4-methyl-1,3-thiazol-5-yl)ethyl}quinoline-5-carboxamide |

TABLE 1-continued

| Compound | Structure | UPAC Name |
|---|---|---|
| 20 | 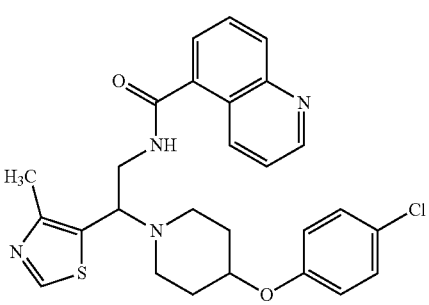 [SMILES: Cc1ncsc1C(CNC(=O)c1cccc2ncccc12)N1CCC(Oc2ccc(Cl)cc2)CC1] | N-{2-[4-(4-chlorophenoxy)piperidin-1-yl]-2-(4-methyl-1,3-thiazol-5-yl)ethyl}quinoline-5-carboxamide |
| 21 | 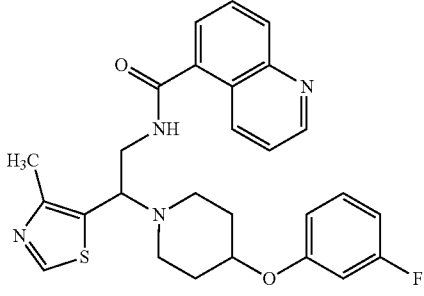 [SMILES: Cc1ncsc1C(CNC(=O)c1cccc2ncccc12)N1CCC(Oc2cccc(F)c2)CC1] | N-{2-[4-(3-fluorophenoxy)piperidin-1-yl]-2-(4-methyl-1,3-thiazol-5-yl)ethyl}quinoline-5-carboxamide |
| 22 | 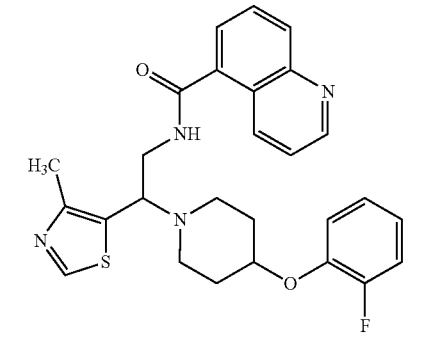 [SMILES: Cc1ncsc1C(CNC(=O)c1cccc2ncccc12)N1CCC(Oc2ccccc2F)CC1] | N-{2-[4-(2-fluorophenoxy)piperidin-1-yl]-2-(4-methyl-1,3-thiazol-5-yl)ethyl}quinoline-5-carboxamide |
| 23 | 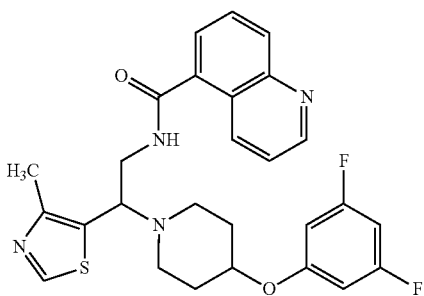 [SMILES: Cc1ncsc1C(CNC(=O)c1cccc2ncccc12)N1CCC(Oc2cc(F)cc(F)c2)CC1] | N-{2-[4-(3,5-difluorophenoxy)piperidin-1-yl]-2-(4-methyl-1,3-thiazol-5-yl)ethyl}quinoline-5-carboxamide |
| 24 | 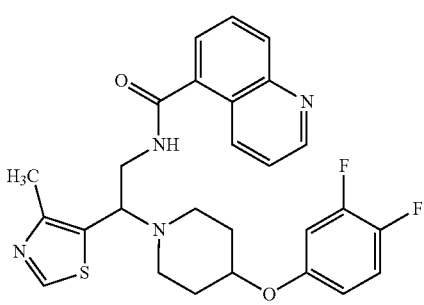 [SMILES: Cc1ncsc1C(CNC(=O)c1cccc2ncccc12)N1CCC(Oc2ccc(F)c(F)c2)CC1] | N-{2-[4-(3,4-difluorophenoxy)piperidin-1-yl]-2-(4-methyl-1,3-thiazol-5-yl)ethyl}quinoline-5-carboxamide |

TABLE 1-continued

| Compound | Structure | UPAC Name |
|---|---|---|
| 25 | 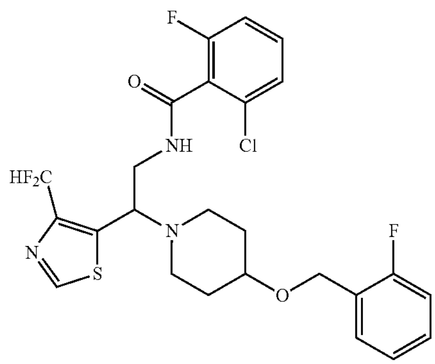 [SMILES: O=C(NCC(c1scnc1C(F)F)N1CCC(OCc2ccccc2F)CC1)c1c(F)cccc1Cl] | 2-chloro-N-{2-[4-(difluoromethyl)-1,3-thiazol-5-yl]-2-{4-[(2-fluorophenyl)methoxy]piperidin-1-yl}ethyl}-6-fluorobenzamide |
| 26 | 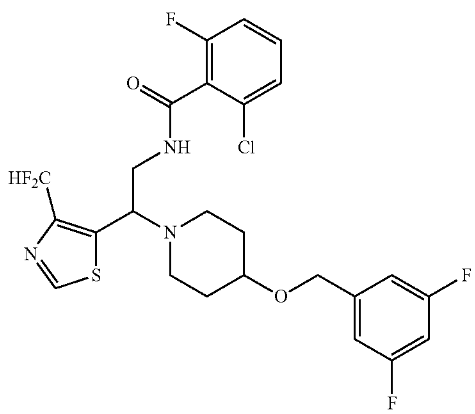 [SMILES: O=C(NCC(c1scnc1C(F)F)N1CCC(OCc2cc(F)cc(F)c2)CC1)c1c(F)cccc1Cl] | 2-chloro-N-{2-[4-(difluoromethyl)-1,3-thiazol-5-yl]-2-{4-[(3,5-difluorophenyl)methoxy]piperidin-1-yl}ethyl}-6-fluorobenzamide |
| 27 | 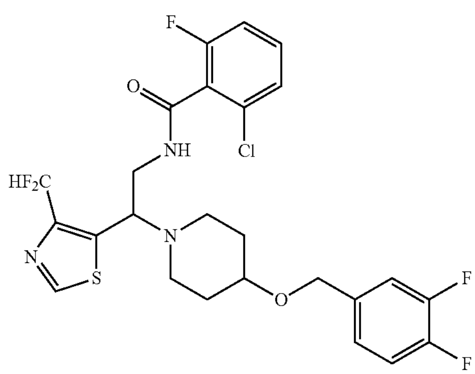 [SMILES: O=C(NCC(c1scnc1C(F)F)N1CCC(OCc2ccc(F)c(F)c2)CC1)c1c(F)cccc1Cl] | 2-chloro-N-{2-[4-(difluoromethyl)-1,3-thiazol-5-yl]-2-{4-[(4,4-difluorophenyl)methoxy]piperidin-1-yl}ethyl}-6-fluorobenzamide |
| 28 | 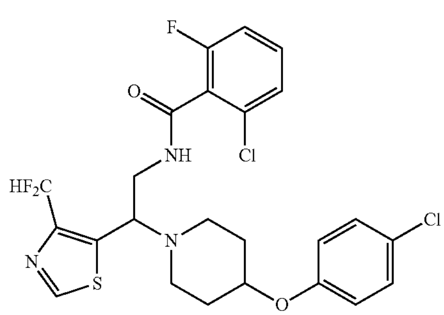 [SMILES: O=C(NCC(c1scnc1C(F)F)N1CCC(Oc2ccc(Cl)cc2)CC1)c1c(F)cccc1Cl] | 2-chloro-N-{2-[4-(4-chlorophenoxy)piperidin-1-yl]-2-[4-(difluoromethyl)-1,3-thiazol-5-yl]ethyl}-6-fluorobenzamide |

TABLE 1-continued

| Compound | Structure | UPAC Name |
|---|---|---|
| 29 | 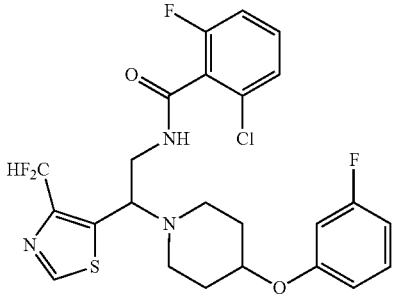 [SMILES: O=C(NCC(c1scnc1C(F)F)N1CCC(Oc2cccc(F)c2)CC1)c1c(F)cccc1Cl] | 2-chloro-N-{2-[4-(difluoromethyl)-1,3-thiazol-5-yl]-2-[4-(3-fluorophenoxy)piperidin-1-yl]ethyl}-6-fluorobenzamide |
| 30 | 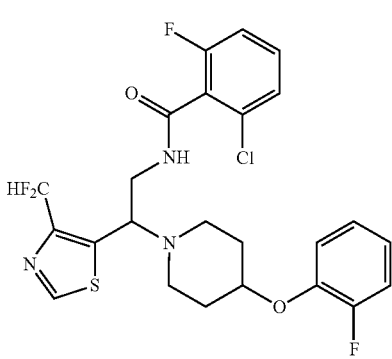 [SMILES: O=C(NCC(c1scnc1C(F)F)N1CCC(Oc2ccccc2F)CC1)c1c(F)cccc1Cl] | 2-chloro-N-{2-[4-(difluoromethyl)-1,3-thiazol-5-yl]-2-[4-(2-fluorophenoxy)piperidin-1-yl]ethyl}-6-fluorobenzamide |
| 31 | 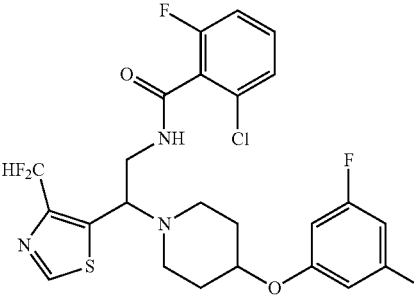 | 2-chloro-N-{2-[4-(difluoromethyl)-1,3-thiazol-5-yl]-2-[4-(3,5-difluorophenoxy)piperidin-1-yl]ethyl}-6-fluorobenzamide |
| 32 | 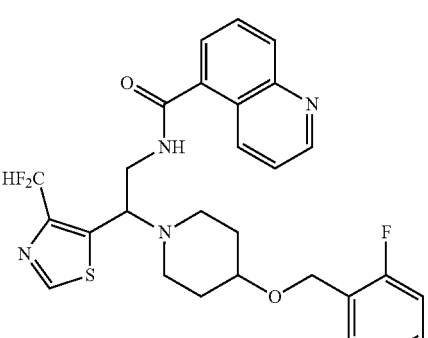 | N-{2-[4-(difluoromethyl)-1,3-thiazol-5-yl]-2-[4-(3,5-fluorophenyl)methoxy]piperidin-1-yl]ethyl}quinoline-5-carboxamide |

TABLE 1-continued

| Compound | Structure | UPAC Name |
|---|---|---|
| 33 | 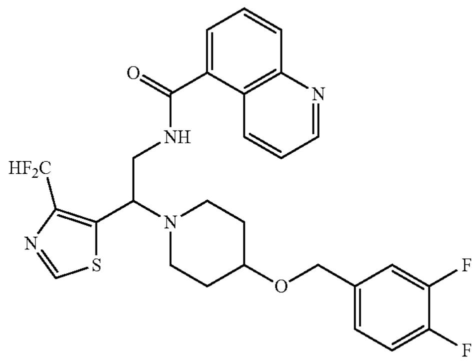 [SMILES: O=C(NCC(c1scnc1C(F)F)N1CCC(OCc2ccc(F)c(F)c2)CC1)c1cccc2ncccc12] | N-{2-[4-(difluoromethyl)-1,3-thiazol-5-yl]-2-{4-[(3,4-difluorophenyl)methoxy]piperidin-1-yl}ethyl}quinoline-5-carboxamide |
| 34 | 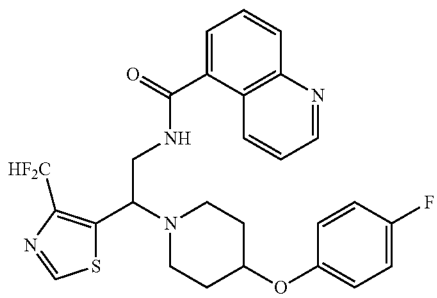 [SMILES: O=C(NCC(c1scnc1C(F)F)N1CCC(Oc2ccc(F)cc2)CC1)c1cccc2ncccc12] | N-{2-[4-(difluoromethyl)-1,3-thiazol-5-yl]-2-[4-(4-fluorophenoxy)piperidin-1-yl]ethyl}quinoline-5-carboxamide |
| 35 | 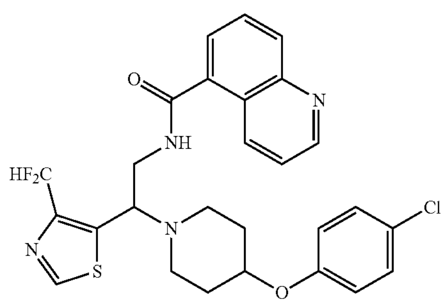 [SMILES: O=C(NCC(c1scnc1C(F)F)N1CCC(Oc2ccc(Cl)cc2)CC1)c1cccc2ncccc12] | N-{2-[4-(4-chlorophenoxy)piperidin-1-yl]-2-[4-(difluoromethyl)-1,3-thiazol-5-yl]ethyl}quinoline-5-carboxamide |
| 36 | 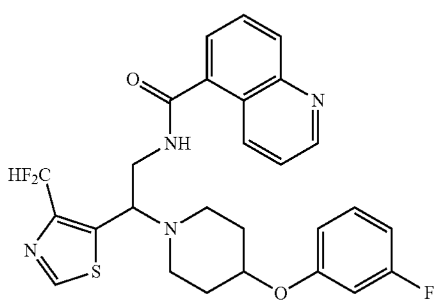 [SMILES: O=C(NCC(c1scnc1C(F)F)N1CCC(Oc2cccc(F)c2)CC1)c1cccc2ncccc12] | N-{2-[4-(difluoromethyl)-1,3-thiazol-5-yl]-2-[4-(3-fluorophenoxy)piperidin-1-yl]ethyl}quinoline-5-carboxamide |
| 37 | 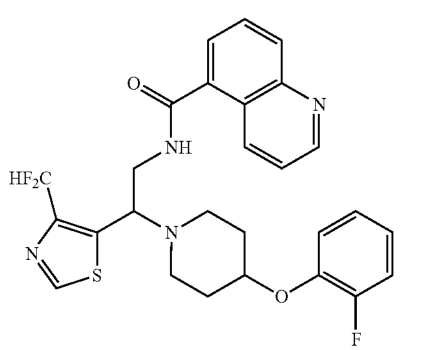 [SMILES: O=C(NCC(c1scnc1C(F)F)N1CCC(Oc2ccccc2F)CC1)c1cccc2ncccc12] | N-{2-[4-(difluoromethyl)-1,3-thiazol-5-yl]-2-[4-(2-fluorophenoxy)piperidin-1-yl]ethyl}quinoline-5-carboxamide |

TABLE 1-continued

| Compound | Structure | UPAC Name |
|---|---|---|
| 38 | 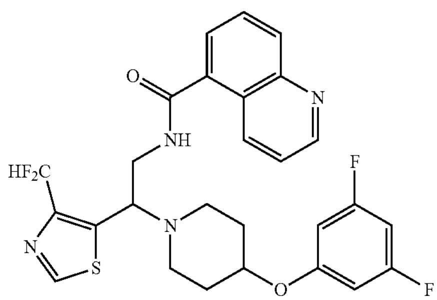 [SMILES: O=C(NCC(c1scnc1C(F)F)N1CCC(Oc2cc(F)cc(F)c2)CC1)c1cccc2ncccc12] | N-{2-[4-(difluoromethyl)-1,3-thiazol-5-yl]-2-[4-(3,5-difluorophenoxy)piperidin-1-yl]ethyl}quinoline-5-carboxamide |

Purification System

Flash Chromatography (FCC)

FCC separations were performed on Interchim puriFlash®430, Interchim puriFlash®450 or Interchim puriFlash® 4250-250 equipped with UV detector. Type of silica columns: Interchim puriFlash® SiHP (high performance silica) 50 μm, 4-25 g.

Supercritical Fluid Chromatography (SFC):

FCC separations were performed on Waters Prep 100q SFC System equipped with Photodiode and MS QDa detectors. Type of silica column: Viridis Prep Silica 2-EP (2-Ethylpyridine) OBD, 19×100 mm, 5 μm. Used method: solvent (A) CO2, solvent (B) methanol; gradient conditions from 5%-10% of B in 8 minutes; ABPR 120 bar; T=40° C.

Analytical Part

LCMS General Procedure

The HPLC measurement was performed using a Dionex Ultimate 3000 module comprising a quaternary pump with degasser, an autosampler, a column oven (set at 25° C.), a diode-array detector DAD (usually wavelength used 200 nm) and a column Kinetex XB C18 4.6×50 mm 2.6 μm. A flow rate of eluaete was 0.5 mL/min. Two mobile phases were used, mobile phase A: 0.1% formic acid in water (MiliQ) solution; mobile phase B: 0.1% formic acid in acetonitrile (HPLC J.T.Baker) solution, and they were employed to run a gradient conditions from 20% B to 80% in 6.7 minutes, hold 80% B for 1.3 minutes, gradient conditions from 80% B to 95% in 0.3 minute, hold 95%B and gradient conditions to 20% B in 0.5 minutes and hold these conditions for 2 minutes in order to reequilibrate the column. An injection volume of 1.0 μl was used. Flow from the column was split to a MS spectrometer. The MS detector (HCT Bruker) was configured with an electrospray ionization source. Mass spectra were acquired by scanning from 100 to 1000 Da. The capillary needle voltage was 4 kV in positive ionization mode and the source temperature was maintained at 365° C. Nitrogen was used as the nebulizer gas the flow was 9.0 l/min. Data acquisition was performed with Data Analysis Bruker Program.

TABLE 2

Retention time ($R_t$) in minutes, [M + H]$^+$ peak for LCMS procedure.

| Compound | $R_t$ [min] | [M + H]$^+$ | λ [nm] |
|---|---|---|---|
| 1 | 4.7 | 506.3 | 200 |
| 2 | 5.1 | 522.3 | 200 |
| 3 | 4.7 | 506.3 | 200 |
| 4 | 4.7 | 506.3 | 200 |
| 5 | 5.0 | 524.4 | 205 |
| 6 | 5.0 | 524.2 | 200 |
| 7 | 4.8 | 492.1 | 200 |
| 8 | 5.4 | 508.2 | 200 |
| 9 | 5.0 | 492.1 | 200 |
| 10 | 4.7 | 492.2 | 220 |
| 11 | 5.3 | 510.3 | 220 |
| 12 | 5.2 | 510.3 | 200 |
| 13 | 3.2 | 505.3 | 205 |
| 14 | 3.9 | 521.3 | 200 |
| 15 | 3.3 | 505.3 | 205 |
| 16 | 3.0 | 505.1 | 205 |
| 17 | 3.8 | 523.1 | 205 |
| 18 | 3.8 | 523.3 | 205 |
| 19 | 3.3 | 491.2 | 205 |
| 20 | 4.3 | 507.3 | 200 |
| 21 | 3.6 | 491.1 | 200 |
| 22 | 3.1 | 491.3 | 200 |
| 23 | 4.1 | 509.1 | 200 |
| 24 | 3.9 | 509.3 | 200 |
| 25 | 6.3 | 542.2 | 200 |
| 26 | 6.9 | 560.2 | 200 |
| 27 | 6.7 | 560.2 | 220 |
| 28 | 7.8 | 544.3 | 200 |
| 29 | 7.3 | 528.2 | 200 |
| 30 | 7.0 | 528.2 | 220 |
| 31 | 7.9 | 546.3 | 200 |
| 32 | 4.7 | 541.3 | 210 |
| 33 | 5.1 | 559.3 | 220 |
| 34 | 5.2 | 527.3 | 210 |
| 35 | 6.0 | 543.3 | 200 |
| 36 | 5.4 | 527.3 | 200 |
| 37 | 5.2 | 527.2 | 230 |
| 38 | 6.0 | 545.3 | 200 |

NMR Characterization $^1$H NMR and $^{13}$C NMR spectra were recorded on a Bruker Avance III HD 400 MHz spectrometer using CDCl$_3$ or CD$_3$OD as a solvent. Chemical shifts (δ) are reported in parts per million (ppm) relative to residual signal of non-fully deuterated solvents pick for $^1$H NMR assigned as 7.26 ppm for CHCl$_3$ and 3.31 ppm for CHD$_2$OD or relative to signal of deuterated solvents pick for $^{13}$C NMR assigned as 77.16 μmm for CHCl$_3$ and 49.00 ppm for CD$_3$OD.

| Compound | ¹H-NMR 400/¹³C-NMR 101 |
|---|---|
| 1 | ¹H NMR (400 MHz, Chloroform-d) δ = 8.70 (s, 1H), 7.32 (td, J = 8.3, 5.9 Hz, 1H), 7.29-7.20 (m, 3H), 7.05 (td, J = 8.6, 1.1 Hz, 1H), 7.03-6.96 (m, 2H), 6.48 (s, 1H), 4.45 (s, 2H), 4.22 (t, J = 7.5 Hz, 1H), 3.83-3.66 (m, 2H), 3.40-3.22 (m, 1H), 2.87-2.75 (m, 2H), 2.48 (s, 3H), 2.37-2.26 (m, 1H), 2.20-2.10 (m, 1H), 2.00-1.87 (m, 2H), 1.74-1.51 ppm (m, 2H). <br> ¹³C NMR (101 MHz, Chloroform-d) δ = 163.62, 162.45, 161.18, 160.99, 158.49, 151.70, 151.18, 134.55, 134.52, 132.52, 132.47, 131.39, 131.30, 129.37, 129.29, 127.24, 125.89, 125.86, 125.36, 125.14, 115.48, 115.27, 114.85, 114.63, 74.31, 69.30, 59.65, 48.69, 45.75, 42.78, 31.78, 31.60, 16.07 ppm. |
| 2 | ¹H NMR (400 MHz, Chloroform-d) δ = 8.71 (s, 1H), 7.47-7.40 (m, 1H), 7.37-7.27 (m, 2H), 7.29-7.15 (m, 4H), 7.05 (td, J = 8.5, 1.0 Hz, 1H), 6.52 (s, 1H), 4.57 (s, 2H), 4.31-4.16 (m, 1H), 3.88-3.65 (m, 2H), 3.52-3.28 (m, 1H), 2.89-2.76 (m, 2H), 2.48 (s, 3H), 2.41-2.30 (m, 1H), 2.26-2.17 (m, 1H), 2.03-1.91 (m, 2H), 1.79-1.61 ppm (m, 2H). <br> ¹³C NMR (101 MHz, Chloroform-d) δ = 162.48, 160.99, 158.49, 151.73, 151.21, 136.51, 132.92, 132.52, 132.47, 131.38, 131.29, 129.37, 129.33, 129.07, 128.72, 126.92, 125.89, 125.85, 125.36, 125.15, 114.85, 114.63, 74.78, 67.16, 59.71, 48.42, 45.89, 42.77, 31.67, 31.53, 16.07ppm. |
| 3 | ¹H NMR (400 MHz, Chloroform-d) δ = 8.70 (s, 114), 7.38-7.19 (m, 3H), 7.10-6.98 (m, 3), 6.94 (ddd, J = 10.6, 8.1, 2.5 Hz, 1H), 6.50 (s, 1H), 4.48 (s, 2H), 4.31-4.16 (m, 1H), 3.83-3.67 (m, 2H), 3.41-3.27 (m, 1H), 2.89-2.71 (m, 2H), 2.48 (s, 3H), 2.38-2.26 (m, 1H), 2.22-2.12 (m, 1H), 2.03-1.84 (m, 2H), 1.78-1.53 ppm (m, 2H). <br> ¹³C NMR (101 MHz, Chloroform-d) δ = 164.31, 162.47, 161.87, 160.98, 158.48, 151.74, 151.23, 141.58, 141.51, 132.51, 132.46, 131.39, 131.30, 130.04, 129.95, 127.18, 125.89, 125.86, 125.35, 125.14, 122.85, 122.82, 114.85, 114.63, 114.58, 114.41, 114.37, 114.19, 74.46, 69.23, 69.21, 59.67, 48.54, 45.77, 42.77, 31.70, 31.53, 16.06 ppm. |
| 4 | ¹H NMR (400 MHz, Chloroform-d) δ = 8.70 (s, 1H), 7.41-7.19 (m, 5H), 7.15-6.97 (m, 3H), 6.50 (s, 1H), 4.55 (s, 2H), 4.29-4.14 (m, 1H), 3.84-3.66 (m, 2H), 3.46-3.27 (m, 1H), 2.92-2.71 (m, 2H), 2.48 (s, 3H), 2.41-2.26 (m, 1H), 2.24-2.09 (m, 1H), 2.03-1.85 (m, 2H), 1.80-1.52 ppm (m, 2H). <br> ¹³C NMR (101 MHz, Chloroform-d) δ = 162.46, 161.96, 160.98, 159.51, 158.48, 151.67, 151.17, 132.51, 132.46, 131.37, 131.28, 129.97, 129.93, 129.39, 129.31, 127.26, 125.94, 125.88, 125.85, 125.80, 125.36, 125.15, 124.24, 124.20, 115.42, 115.21, 114.85, 114.63, 74.57, 63.47, 63.43, 59.66, 48.60, 45.77, 42.76, 31.72, 31.56, 16.06 ppm. |
| 5 | ¹H NMR (400 MHz, Chloroform-d) δ = 8.71 (s, 1H), 7.38-7.28 (m, 1H), 7.28-7.19 (m, 2H), 7.05 (td, J = 8.5, 1.0 Hz, 1H), 6.89-6.75 (m, 2H), 6.69 (td, J = 8.8, 4.3 Hz, 1H), 6.47 (s, 1H), 4.46 (s, 2H), 4.30-4.16 (m, 1H), 3.86-3.63 (m, 2H), 3.44-3.22 (m, 1H), 2.91-2.72 (m, 2H), 2.48 (s, 3H), 2.40-2.26 (m, 1H), 2.25-2.11 (m, 1H), 2.03-1.84 (m, 2H), 1.79-1.50 ppm (m, 2H). <br> ¹³C NMR (101 MHz, Chloroform-d) δ = 164.49, 164.37, 162.48, 162.02, 161.90, 158.47, 151.21, 132.50, 132.44, 131.42, 131.32, 127.20, 125.89, 125.85, 114.85, 114.63, 109.95, 109.88, 109.76, 109.70, 102.86, 74.77, 68.77, 59.68, 48.50, 45.74, 42.77, 31.68, 31.52, 16.07 ppm. |
| 6 | ¹H NMR (400 MHz, Chloroform-d) δ = 8.71 (s, 1H), 7.37-7.28 (m, 1H), 7.28-7.20 (m, 1H), 7.17-7.02 (m, 3H), 7.02-6.95 (m, 1H), 6.47 (s, 1H), 4.43 (s, 2H), 4.29-4.16 (m, 1H), 3.83-3.68 (m, 2H), 3.38-3.25 (m, 1H), 2.87-2.74 (m, 2H), 2.48 (s, 3H), 2.39-2.27 (m, 1H), 2.23-2.10 (m, 1H), 2.01-1.86 (m, 2H), 1.75-1.52 ppm (m, 2H). <br> ¹³C NMR (101 MHz, Chloroform-d) δ = 164.49, 164.37, 162.48, 162.02, 161.90, 160.97, 158.47, 151.71, 151.21, 132.50, 131.42, 131.32, 127.20, 125.89, 125.85, 114.85, 114.63, 109.95, 109.88, 109.76, 109.70, 102.86, 102.61, 74.77, 68.77, 59.68, 48.50, 45.74, 42.77, 31.68, 31.52, 16.07 ppm. |
| 7 | ¹H NMR (400 MHz, Chloroform-d) δ = 8.73 (s, 1H), 7.38-7.28 (m, 1H), 7.28-7.19 (m, 1H), 7.11-701 (m, 1H), 6.98-6.88 (m, 2H), 6.82-6.73 (m, 2H), 6.47 (s, 1H), 4.31-4.21 (m, 1H), 4.21-4.08 (m, 1H), 3.88-3.66 (m, 2H), 2.87-2.76 (m, 2H), 2.50 (s, 3H), 2.48-2.40 (m, 1H), 2.40-2.28 (m, 1H), 2.06-1.91 (m, 1H), 1.87-1.58 ppm (m, 2H). <br> ¹³C NMR (101 MHz, Chloroform-d) δ = 162.53, 161.70, 160.98, 158.73, 158.49, 156.35, 153.39, 153.37, 151.35, 132.50, 132.45, 131.45, 131.36, 125.91, 125.87, 125.29, 125.08, 117.64, 117.56, 116.14, 115.91, 114.87, 114.65, 73.48, 59.87, 47.56, 45.99, 42.81, 31.20, 31.11, 16.08 ppm. |
| 8 | ¹H NMR (400 MHz, Chloroform-0 6 = 8.72 (s, 1H), 7.37-7.29 (m, 1H), 7.28-7.22 (m, 1H), 7.22-7.14 (m, 2H), 7.10-7.02 (m, 1H), 6.80-6.73 (m, 2H), 6.43 (s, 1H), 4.30-4.14 (m, 2H), 3.87-3.68 (m, 2H), 2.87-2.72 (m, 2H), 2.49 (s, 3H), 2.47-2.39 (m, 1H), 2.37-2.28 (m, 1H), 2.03-1.92 (m, 2H), 1.87-1.69 ppm (m, 2H). <br> ¹³C NMR (101 MHz, Chloroform-d) δ = 162.47, 160.99, 158.49, 155.96, 152.62, 151.80, 151.29, 132.52, 132.47, 131.42, 131.33, 129.55, 127.28, 125.93, 125.90, 125.87, 125.33, 125.11, 117.47, 114.86, 114.64, 72.99, 59.82, 47.54, 45.92, 42.82, 31.17, 31.07, 16.08 ppm. |
| 9 | ¹H NMR (400 MHz, Chloroform-d) δ = 8.73 (s, 1H), 7.39-7.28 (m, 1H), 7.29-7.20 (m, 1H), 7.23-7.12 (m, 1H), 7.11-7.02 (m, 1H), 6.67-6.57 (m, 2H), 6.59-6.50 (m, 1H), 6.44 (s, 1H), 4.33-4.12 (m, 1H), 3.87-3.67 (m, 1H), 3.49 (s, 2H), 2.88-2.72 (m, 2H), 2.50 (s, 3H), 2.49-2.40 (m, 1H), 2.40-2.30 (m, 1H), 2.08-1.92 (m, 2H), 1.91-1.71 ppm (m, 2H). <br> ¹³C NMR (101 MHz, Chloroform-0 6 = 165.03, 162.59, 162.49, 161.00, 158.83, 158.72, 158.50, 151.83, 151.32, 132.53, 132.48, 131.43, 131.34, 131.02, 130.44, 130.34, 127.24, 125.91, 125.87, 125.33, 125.12, 114.86, 114.65, 111.74, 111.71, 107.94, 107.73, 103.75, 103.51, 72.80, 59.84, 47.52, 45.95, 42.83, 31.14, 31.05, 16.08 ppm. |
| 10 | ¹H NMR (400 MHz, Chloroform-d) δ = 8.73 (s, 1H), 7.38-7.28 (m, 1H), 7.28-7.20 (m, 1H), 7.11-6.97 (m, 3H), 6.96-6.87 (m, 2H), 6.52 (s, 1H), 4.34-4.24 (m, 1H), 4.24-4.11 (m, 1H), 3.88-3.68 (m, 2H), 2.92-2.79 (m, 2H), 2.50 (s, 3H), 2.49-2.39 (m, 1H), 2.39-2.27 (m, 1H), 2.10-1.95 (m, 2H), 1.93-1.75 ppm (m, 2H). <br> ¹³C NMR (101 1V11-1z, Chloroform-d) δ = 162.52, 160.98, 158.48, 155.34, 152.90, 151.39, 145.26, 145.15, 132.51, 132.46, 131.42, 131.32, 125.90, 125.87, 125.32, 125.10, 124.42, 124.38, 122.37, 122.30, 118.77, 118.75, 116.84, 116.66, 114.86, 114.64, 75.11, 59.81, 47.74, 45.81, 42.78, 31.34, 31.21, 16.07 ppm. |
| 11 | ¹H NMR (400 MHz, Chloroform-d) δ = 8.73 (s, 1H), 7.38-7.29 (m, 1H), 7.28-7.20 (m, 1H), 7.06 (td, J = 8.5, 1.0 Hz, 1H), 6.45-6.31 (m, 4H), 4.29-4.21 (m, 1H),4.21-4.12 (m, 1H), 3.88-3.78 (m, 1H), 3.78-3.67 (m, 1H), 2.87-2.71 (m, 2H), 2.50 (s, 3H), 2.48-2.41 (m, 1H), 2.41-2.29 (m, 1H), 2.12-1.89 (m, 2H), 1.91-1.69 ppm (m, 2H). <br> ¹³C NMR (101 MHz, Chloroform-d) δ = 165.18, 165.02, 162.73, 162.57, 162.47, 160.99, 159.52, 159.38, 159.25, 158.49, 151.84, 151.33, 132.53, 132.47, 131.44, 131.35, 127.25, 125.91, 125.88, 125.32, 125.10, 114.87, 114.65, 99.63, 99.55, 99.43, 99.35, 96.83, 96.57, 96.31, 73.20, 59.84, 47.39, 45.89, 42.84, 31.01, 30.93, 16.09 ppm. |
| 12 | ¹H NMR (400 MHz, Chloroform-d) δ = 8.73 (s, 1H), 7.38-7.28 (m, 1H), 7.28-7.19 (m, 1H), 7.14-6.97 (m, 2H), 6.71-6.62 (m, 1H), 6.57-6.50 (m, 1H), 6.42 (s, 1H), 4.32-4.20 (m, 1H), 4.19-4.07 (m, 1H), 3.92-3.79 (m, 1H), 3.78-3.67 (m, 1H), 2.87-2.72 (m, 2H), 2.50 (s, 3H), 2.48-2.39 (m, 1H), 2.40-2.27 (m, 1H), 2.10-1.89 (m, 2H), 1.91-1.70 ppm (m, 2H). <br> ¹³C NMR (101 MHz, Chloroform-d) δ = 162.48, 160.99, 158.49, 153.59, 151.94, 151.81, 151.34, 149.48, 149.34, 148.61, 132.53, 132.47, 131.44, 131.34, 130.82, 127.30, 125.91, 125.87, 125.31, 125.10, 117.49, 117.30, 114.86, 114.64, 111.68, 111.64, 111.62, 111.58, 105.91, 105.71, 73.63, 59.86, 47.45, 45.94, 42.84, 31.06, 31.00, 16.08 ppm. |
| 13 | ¹H NMR (400 MHz, Chloroform-d) δ = 8.96 (dd, J = 4.2, 1.7 Hz, 1H), 8.78 (ddd, J = 8.6, 1.7, 0.8 Hz, 1H), 8.72 (s, 1H), 8.22 (dt, J = 8.4, 1.1 Hz, 1H), 7.76-7.68 (m, 1H), 7.65 (dd, J = 7.1, 1.3 Hz, 1H), 7.47 (dd, J = 8.6, 4.2 Hz, 1H), 7.30-7.22 (m, 2H), 7.05-6.95 (m, 2H), 6.64 (s, 1H), 4.46 (s, 2H), 4.32-4.17 (m, 1H), 3.88-3.77 (m, 1H), 3.42-3.30 (m, 1H), 2.93-2.80 (m, 2H), 2.49 (s, 3H), 2.40-2.28 (m, 1H), 2.29-2.16 (m, 1H), 2.02-1.88 (m, 2H), 1.76-1.56 ppm (m, 1H). <br> ¹³C NMR (101 MHz, Chloroform-d) δ = 168.23, 167.89, 163.63, 161.19, 151.53, 151.28, 151.14, 148.47, 134.51, 134.48, 134.25, 134.12, 132.72, 131.01, 129.37, 129.29, 128.95, 128.46, 127.82, 125.98, 125.48, 122.17, 115.50, 115.29, 74.19, 69.34, 60.08, 48.71, 46.27, 42.79, 31.83, 31.69, 16.09 ppm. |
| 14 | ¹H NMR (400 MHz, Chloroform-d) δ = 8.96 (dd, J = 4.2, 1.7 Hz, 1H), 8.83-8.75 (m, 1H), 8.72 (s, 1H), 8.21 (dt, J = 8.3, 1.1 Hz, 1H), 7.75-7.69 (m, 1H), 7.66 (d, J = 7.0 Hz, 1H), 7.47 (dd, J = 8.6, 4.2 Hz, 1H), 7.46-7.42 (m, 1H), 7.32 (dd, J = 7.5, 1.7 |

| Compound | ¹H-NMR 400/¹³C-NMR 101 |
|---|---|
| | Hz, 1H), 7.25-7.18 (m, 2H), 6.66 (s, 1H), 4.58 (s, 2H), 4.33-4.20 (m, 1H), 3.90-3.74 (m, 2H), 3.50-3.35 (m, 1H), 2.92-2.82 (m, 2H), 2.49 (s, 3H), 2.44-2.34 (m, 1H), 2.32-2.23 (m, 1H), 2.07-1.93 (m, 2H), 1.82-1.60 ppm (m, 2H).<br>¹³C NMR (101 MHz, Chloroform-d) δ = 168.25, 151.56, 151.30, 151.12, 148.47, 136.47, 134.25, 134.11, 132.93, 132.70, 129.39, 129.09, 128.76, 128.46, 127.77, 126.93, 125.98, 125.51, 122.16, 74.68, 67.20, 60.13, 48.50, 46.36, 42.78, 31.74, 31.62, 16.09 ppm. |
| 15 | ¹H NMR (400 MHz, Chloroform-d) δ = 8.96 (dd, J = 4.2, 1.7 Hz, 1H), 8.78 (ddd, J = 8.7, 1.7, 0.9 Hz, 1H), 8.72 (s, 1H), 8.22 (dt, J = 8.4, 1.1 Hz, 1H), 7.72 (dd, J = 8.4, 7.1 Hz, 1H), 7.66 (dd, J = 7.1, 1.3 Hz, 1H), 7.48 (dd, J = 8.6, 4.2 Hz, 1H), 7.32-7.23 (m, 1H), 7.11-7.00 (m, 2H), 6.95 (ddd, J = 10.6, 8.0, 2.5 Hz, 1H), 6.64 (s, 1H), 4.49 (s, 2H), 4.33-4.19 (m, 1H), 3.90-3.75 (m, 2H), 3.44-3.28 (m, 1H), 2.91-2.79 (m, 2H), 2.49 (s, 3H), 2.43-2.30 (m, 1H), 2.30-2.16 (m, 1H), 2.02-1.87 (m, 2H), 1.81-1.53 ppm (m, 2H).<br>¹³C NMR (101 MHz, Chloroform-d) δ = 168.23, 164.32, 161.88, 151.52, 151.28, 151.14, 148.49, 141.56, 141.49, 134.24, 134.13, 132.73, 131.01, 130.06, 129.97, 128.46, 127.82, 125.98, 125.48, 122.85, 122.83, 122.16, 114.61, 114.41, 114.40, 114.20, 74.38, 69.26, 60.09, 48.65, 46.26, 42.79, 31.80, 31.67, 16.09 ppm. |
| 16 | ¹H NMR (400 MHz, Chloroform-d) δ = 8.96 (dd, J = 4.2, 1.7 Hz, 1H), 8.83-8.75 (m, 1H), 8.72 (s, 1H), 8.25-8.19 (m, 1H), 7.72 (dd, J = 8.4, 7.0 Hz, 1H), 7.66 (dd, J = 7.1, 1.4 Hz, 1H), 7.48 (dd, J = 8.6, 4.2 Hz, 1H), 7.38 (td, J = 7.5, 1.8 Hz, 1H), 7.30-7.19 (m, 1H), 7.11 (td, J = 7.5, 1.2 Hz, 1H), 7.01 (ddd, J = 9.7, 8.2, 1.2 Hz, 1H), 6.65 (s, 1H), 4.56 (s, 2H), 4.30-4.17 (m, 1H), 3.89-3.77 (m, 2H), 3.46-3.32 (m, 1H), 2.93-2.78 (m, 2H), 2.49 (s, 3H), 2.45-2.29 (m, 1H), 2.29-2.14 (m, 1H), 1.95 (d, J = 14.0 Hz, 2H), 1.76-1.56 ppm (m, 2H).<br>¹³C NMR (101 MHz, Chloroform-d) δ = 168.22, 167.89, 161.97, 159.52, 151.49, 151.25, 151.13, 148.48, 134.26, 134.14, 132.71, 132.62, 131.01, 129.99, 129.95, 129.43, 129.35, 128.95, 128.47, 127.86, 125.95, 125.92, 125.78, 125.49, 124.25, 124.22, 122.16, 115.44, 115.23, 74.47, 68.31, 60.07, 48.68, 46.26, 42.79, 31.80, 31.66, 16.08 ppm. |
| 17 | ¹H NMR (400 MHz, Chloroform-d) δ = 8.96 (dd, J = 4.2, 1.7 Hz, 1H), 8.77 (ddd, J = 8.6, 1.7, 0.9 Hz, 1H), 8.73 (s, 1H), 8.22 (dt, J = 8.4, 1.1 Hz, 1H), 7.72 (dd, J = 8.4, 7.1 Hz, 1H), 7.66 (dd, J = 7.1, 1.4 Hz, 1H), 7.47 (dd, J = 8.6, 4.2 Hz, 1H), 6.88-6.79 (m, 2H), 6.75-6.66 (m, 1H), 6.63 (s, 1H), 4.47 (s, 2H), 4.32-4.23 (m, 1H), 3.91-3.75 (m, 2H), 3.43-3.31 (m, 1H), 2.93-2.78 (m, 2H), 2.49 (s, 3H), 2.43-2.33 (m, 1H), 2.31-2.18 (m, 1H), 2.03-1.89 (m, 2H), 1.81-1.52 ppm (m, 2H).<br>¹³C NMR (101 MHz, Chloroform-d) δ = 168.28, 164.51, 164.38, 162.04, 161.91, 152.07, 151.62, 151.35, 151.14, 148.48, 143.14, 143.06, 134.22, 134.08, 132.74, 131.01, 128.94, 128.45, 127.73, 125.98, 125.50, 122.16, 109.96, 109.89, 109.77, 109.70, 103.14, 102.89, 102.64, 74.57, 68.81, 60.16, 48.50, 46.32, 42.81, 31.69, 31.57, 16.08 ppm. |
| 18 | ¹H NMR (400 MHz, Chloroform-d) δ = 8.96 (dd, J = 4.2, 1.7 Hz, 1H), 8.81-8.75 (m, 1H), 8.73 (s, 1H), 8.28-8.16 (m, 1H), 7.72 (dd, J = 8.4, 7.1 Hz, 1H), 7.65 (dd, J = 7.2, 1.3 Hz, 1H), 7.48 (dd, J = 8.6, 4.2 Hz, 1H), 7.21-7.04 (m, 2H), 7.00 (d, J = 4.5 Hz, 1H), 6.62 (s, 1H), 4.44 (s, 2H), 4.32-4.19 (m, 1H), 3.98-3.76 (m, 2H), 3.46-3.26 (m, 1H), 2.97-2.76 (m, 2H), 2.49 (s, 3H), 2.45-2.28 (m, 1H), 2.29-2.17 (m, 1H), 2.03-1.84 (m, 2H), 1.79-1.54 pm (m, 2H).<br>¹³C NMR (101 MHz, Chloroform-d) δ = 168.23, 151.53, 151.32, 151.13, 148.45, 135.94, 135.90, 135.89, 135.85, 134.26, 134.12, 132.71, 128.46, 127.83, 125.98, 125.48, 123.28, 123.25, 123.22, 123.18, 122.17, 117.32, 117.15, 116.52, 116.34, 74.46, 68.80, 60.10, 48.57, 46.27, 42.80, 31.77, 31.64, 16.09 ppm. |
| 19 | ¹H NMR (400 MHz, Chloroform-d) δ = 8.97 (dd, J = 4.2, 1.7 Hz, 1H), 8.77 (ddd, J = 8.6, 1.7, 0.8 Hz, 1H), 8.74 (s, 1H), 8.23 (dt, J = 8.4, 1.1 Hz, 1H), 7.73 (dd, J = 8.4, 7.1 Hz, 1H), 7.66 (dd, J = 7.1, 1.3 Hz, 1H), 7.48 (dd, J = 8.6, 4.2 Hz, 1H), 7.00-6.88 (m, 2H), 6.86-6.74 (m, 2H), 6.60 (s, 1H), 4.33-4.24 (m, 1H), 4.21-4.11 (m, 1H), 3.96-3.84 (m, 1H), 3.85-3.76 (m, 1H), 2.93-2.72 (m, 2H), 2.51 (s, 3H), 2.49-2.28 (m, 1H), 2.10-1.92 (m, 2H), 1.89-1.71 ppm (m, 2H).<br>¹³C NMR (101 MHz, Chloroform-d) δ = 168.28, 158.75, 157.18, 156.37, 153.37, 153.35, 151.40, 151.17, 148.49, 134.22, 134.11, 132.76, 128.45, 127.81, 125.99, 125.49, 122.18, 117.66, 117.58, 116.17, 115.94, 73.38, 60.24, 47.71, 46.36, 42.83, 31.30, 31.22, 16.11 ppm. |
| 20 | ¹H NMR (400 MHz, Methanol-d₄) δ = 8.96 (s, 1H), 8.90 (dd, J = 4.3, 1.7 Hz, 1H), 8.57 (ddd, J = 8.6, 1.7, 0.9 Hz, 1H), 8.13 (dt, J = 8.6, 1.1 Hz, 1H), 7.80 (dd, J = 8.6, 7.1 Hz, 1H), 7.64 (dd, J = 7.1, 1.2 Hz, 1H), 7.58 (dd, J = 8.6, 4.3 Hz, 1H), 7.26-7.17 (m, 2H), 6.95-6.84 (m, 2H), 4.45 (t, J = 7.3 Hz, 1H), 4.38-4.29 (m, 1H), 4.08-3.98 (m, 1H), 3.67-3.63 (m, 1H), 3.01-2.83 (m, 2H), 2.60-2.45 (m, 2H), 2.46 (s, 3H), 2.15-1.98 (m, 2H), 1.89-1.71 ppm (m, 2H).<br>¹³C NMR (101 MHz, Methanol-d₄) δ = 170.71, 157.56, 153.78, 152.41, 151.79, 148.67, 135.94, 131.74, 130.89, 130.35, 130.15, 127.23, 126.87, 126.57, 123.17, 118.54, 74.03, 61.64, 55.09, 47.88, 44.39, 32.16, 32.08, 15.65 ppm. |
| 21 | ¹H NMR (400 MHz, Chloroform-d) δ = 8.97 (dd, J = 4.2, 1.7 Hz, 1H), 8.78 (dd, J = 1.7, 0.9 Hz, 1H), 8.75 (s, 1H), 8.23 (dt, J = 8.4, 1.1 Hz, 1H), 7.73 (dd, J = 8.4, 7.1 Hz, 1H), 7.66 (dd, J = 7.0, 1.3 Hz, 1H), 7.48 (dd, J = 8.6, 4.2 Hz, 1H), 7.24-7.10 (m, 1H), 6.71-6.48 (m, 4H), 4.34-4.15 (m, 2H), 3.97-3.86 (m, 1H), 3.86-3.73 (m, 2H), 2.94-2.77 (m, 2H), 2.51 (s, 3H), 2.53-2.35 (m, 2H), 2.10-1.93 (m, 2H), 1.83 ppm (dq, J = 11.8, 8.3, 7.5 Hz, 2H).<br>¹³C NMR (101 MHz, Chloroform-d) δ = 168.26, 165.03, 162.59, 158.79, 158.69, 151.63, 151.41, 151.15, 148.46, 134.24, 134.12, 132.73, 130.46, 130.37, 128.46, 127.88, 125.99, 125.48, 122.19, 111.76, 111.73, 108.00, 107.78, 103.76, 103.52, 72.67, 60.24, 47.67, 46.35, 42.83, 31.20, 31.13, 16.11 ppm. |
| 22 | ¹H NMR (400 MHz, Chloroform-d) δ = 8.97 (dd, J = 4.2, 1.7 Hz, 1H), 8.79 (dd, J = 1.8, 0.9 Hz, 1H), 8.74 (s, 1H), 8.22 (dt, J = 8.4, 1.1 Hz, 1H), 7.73 (dd, J = 8.4, 7.1 Hz, 1H), 7.66 (dd, J = 7.1, 1.3 Hz, 1H), 7.48 (dd, J = 8.7, 4.2 Hz, 1H), 7.10-6.98 (m, 2H), 6.98-6.85 (m, 2H), 6.63 (s, 1H), 4.33-4.25 (m, 1H), 3.97-3.76 (m, 2H), 2.97-2.84 (m, 2H), 2.50 (s, 3H), 2.54-4.27-4.18 (m,2.28 (m, 2H), 2.11-1.94 (m, 2H), 1.94-1.78 ppm (m, 2H).<br>¹³C NMR (101 MHz, Chloroform-d) δ = 6 168.27, 155.37, 152.93, 151.58, 151.38, 151.13, 148.45, 145.25, 145.14, 134.26, 134.10, 132.71, 128.48, 127.89, 125.98, 125.50, 124.42, 124.38, 122.42, 122.35, 122.18, 118.85, 116.86, 116.67, 75.10, 60.17, 47.99, 46.18, 42.80, 31.48, 31.38, 16.09 pm. |
| 23 | ¹H NMR (400 MHz, Chloroform-d) δ = 8.97 (dd, J = 4.2, 1.7 Hz, 1H), 8.78-8.74 (m, 2H), 8.23 (dt, J = 8.5, 1.1 Hz, 1H), 7.78-7.70 (m, 1H), 7.65 (dd, J = 7.1, 1.3 Hz, 1H), 7.48 (dd, J = 8.6, 4.2 Hz, 1H), 6.56 (s, 1H), 6.45-6.32 (m, 3H), 4.35-4.25 (m, 1H), 4.24-4.14 (m, 1H), 3.97-3.85 (m, 1H), 3.83-3.65 (m, 1H), 2.91-2.75 (m, 2H), 2.51 (s, 3H), 2.}-2.35 (m, 2H), 2.09-1.62 ppm (m, 4H).<br>¹³C NMR (101 MHz, Chloroform-d) δ = 168.29, 165.03, 162.74, 159.34, 151.66, 151.47, 151.15, 148.44, 134.24, 134.10, 132.72, 131.02, 128.95, 128.47, 127.87, 125.98, 125.49, 122.20, 99.65, 99.38, 96.63, 73.02, 60.25, 47.56, 46.33, 42.86, 31.05, 30.99, 16.09 ppm. |
| 24 | ¹H NMR (400 MHz, Chloroform-d) δ = 8.96 (dd, J = 4.2, 1.7 Hz, 1H), 8.79-8.71 (m, 2H), 8.22 (dt, J = 8.4, 1.1 Hz, 1H), 7.72 (dd, J = 8.4, 7.1 Hz, 1H), 7.65 (dd, J = 7.1, 1.3 Hz, 1H), 7.47 (dd, J = 8.6, 4.2 Hz, 1H), 7.02 (dt, J = 10.0, 9.1 Hz, 1H), 6.66 (ddd, J = 12.0, 6.6, 3.0 Hz, 1H), 6.63-6.47 (m, 2H), 4.36-4.24 (m, 1H), 4.22-4.12 (m, 1H), 4.00-3.85 (m, 1H), 3.85-3.74 (m, 1H), 2.91-2.78 (m, 2H), 2.50 (s, 3H), 2.43 (d, J = 24.7 Hz, 2H), 2.05-1.92 (m, 2H), 1.88-1.71 ppm (m, 2H).<br>¹³C NMR (101 MHz, Chloroform-d) δ = 168.27, 153.65, 153.62, 153.56, 153.54, 151.94, 151.80, 151.65, 151.42, 151.15, 149.47, 149.34, 148.46, 146.51, 144.12, 143.99, 134.19, 134.09, 132.73, 128.42, 127.86, 125.96, 125.47, 122.17, 117.50, 117.49, 117.32, 117.30, 111.70, 111.66, 111.64, 111.60, 105.91, 105.75, 73.48, 60.25, 47.61, 46.33, 42.85, 31.14, 31.07, 16.09 ppm. |
| 25 | ¹H NMR (400 MHz, Chloroform-d) δ = 8.77 (s, 1H), 7.42-7.36 (m, 1H), 7.36-7.29 (m, 1H), 7.29-7.19 (m, 2H), 7.16-7.08 (m, 1H), 7.08-6.97 (m, 2H), 6.92 (t, J = 54.1 Hz, 1H), 6.38 (s, 1H), 4.62-4.56 (m, 1H), 4.56 (s, 2H), 3.90-3.70 (m, 1H), 3.45-3.33 (m, 1H), 2.93-2.84 (m, 1H), 2.84-2.72 (m, 1H), 2.41-2.20 (m, 2H), 2.04-1.88 (m, 2H), 1.79-1.59 ppm (m, 2H).<br>¹³C NMR (101 MHz, Chloroform-d) δ = 162.52, 161.97, 160.96, 159.52, 158.46, 152.93, 137.22, 132.53, 132.47, 131.45, 131.36, 129.98, 129.93, 129.40, 129.32, 125.90, 125.86, 125.79, 125.17, |

| Compound | ¹H-NMR 400/¹³C-NMR 101 |
|---|---|
| | 124.96, 124.25, 124.21, 115.43, 115.22, 114.84, 114.63, 114.03, 111.67, 109.31, 74.36, 63.52, 58.75, 48.23, 46.45, 42.97, 31.61, 31.48 ppm. |
| 26 | ¹H NMR (400 MHz, Chloroform-d) δ = 8.78 (d, J = 0.8 Hz, 1H), 7.37-7.29 (m, 1H), 7.25-7.20 (m, 1H), 7.10-7.02 (m, 1H), 6.92 (t, J = 54.5 Hz, 1H), 6.88-6.77 (m, 2H), 6.73-6.64 (m, 1H), 6.36 (s, 114), 4.66-4.56 (m, 1H), 4.47 (s, 2H), 3.89-3.70 (m, 2H), 3.46-3.32 (m, 1H), 2.93-2.84 (m, 1H), 2.84-2.75 (m, 1H), 2.41-2.21 (m, 2H), 2.02-1.88 (m, 2H), 1.77-1.56 (m, 2H). ¹³C NMR (101 MHz, Chloroform-d) δ = 164.49, 164.37, 162.51, 162.03, 161.90, 160.95, 158.45, 152.95, 147.64, 147.38, 147.12, 143.18, 143.09, 143.00, 137.14, 132.51, 132.46, 131.48, 131.39, 125.90, 125.87, 125.14, 124.93, 114.85, 114.63, 114.05, 111.69, 109.95, 109.88, 109.77, 109.70, 109.33, 103.11, 102.86, 102.60, 74.55, 68.79, 68.77, 68.74, 58.75, 48.09, 46.40, 42.97, 31.57, 31.44. |
| 27 | ¹H NMR (400 MHz, Chloroform-d) δ = 8.78 (s, 1H), 7.37-7.29 (m, 1H), 7.24-7.20 (m, 1H), 7.18-7.10 (m, 2H), 7.10-6.96 (m, 2H), 6.92 (t, J = 54.1 Hz, 1H), 6.35 (s, 1H), 4.65-4.51 (m, 1H), 4.44 (s, 2H), 3.91-3.73 (m, 2H), 3.42-3.30 (m, 1H), 2.94-2.84 (m, 1H), 2.84-2.70 (m, 1H), 2.42-2.22 (m, 2H), 2.00-1.89 (m, 2H), 1.78-1.55 ppm (m, 2H). ¹³C NMR (101 MHz, Chloroform-d) δ = 162.52, 160.95, 158.45, 152.96, 151.78, 151.65, 149.31, 149.19, 148.68, 148.56, 137.18, 135.92, 132.52, 132.47, 131.48, 131.39, 125.90, 125.87, 125.14, 124.93, 123.28, 123.25, 123.22, 123.18, 117.31, 117.14, 116.51, 116.34, 114.85, 114.63, 114.05, 111.69, 109.32, 74.36, 68.78, 58.78, 48.16, 46.45, 42.97, 31.60, 31.47 ppm. |
| 28 | ¹H NMR (400 MHz, Chloroform-d) δ = 8.80 (s, 1H), 7.37-7.29 (m, 1H), 7.25-7.17 (m, 3H), 7.11-7.01 (m, 1H), 6.94 (t, J = 54.2 Hz, 1H), 6.81-6.74 (m, 2H), 6.36 (s, 1H), 4.73-4.58 (m, 1H), 4.29-4.18 (m, 1H), 3.89-3.77 (m, 2H), 2.95-2.74 (m, 2H), 2.55-2.35 (m, 2H), 2.09-1.91 (m, 2H), 1.90-1.66 ppm (m, 2H). ¹³C NMR (101 MHz, Chloroform-d) δ = 162.54, 160.96, 158.46, 155.92, 153.07, 147.51, 147.13, 132.53, 132.48, 131.50, 131.40, 129.57, 126.00, 125.91, 125.88, 125.13, 124.92, 117.51, 114.85, 114.64, 114.09, 111.73, 109.36, 72.67, 58.93, 47.29, 46.42, 42.97, 30.99, 30.93 ppm. |
| 29 | ¹H NMR (400 MHz, Chloroform-d) δ = 8.80 (s, 1H), 7.38-7.29 (m, 1H), 7.27-7.14 (m, 4H), 7.10-7.02 (m, 1H), 6.94 (t, J = 54.1 Hz, 1H), 6.68-6.60 (m, 2H), 6.60-6.52 (m, 1H), 6.33 (s, 1H), 4.69-4.54 (m, 1H), 4.31-4.18 (m, 1H), 3.88-3.73 (m, 2H), 2.92-2.75 (m, 2H), 2.52-2.35 (m, 2H), 2.06-1.93 (m, 2H), 1.93-1.72 pm (m, 2H). ¹³C NMR (101 MHz, Chloroform-d) δ = 165.03, 162.60, 162.52, 160.97, 158.81, 158.70, 158.47, 153.01, 147.47, 147.22, 137.22, 132.54, 132.48, 131.50, 131.41, 130.46, 130.35, 125.92, 125.88, 125.15, 124.94, 114.86, 114.64, 114.10, 111.75, 111.72, 109.38, 107.98, 107.76, 103.78, 103.54, 72.58, 58.89, 47.31, 46.38, 43.00, 31.05, 30.98 ppm. |
| 30 | ¹H NMR (400 MHz, Chloroform-d) δ = 8.79 (s, 1H), 7.37-7.30 (m, 1H), 7.26-7.20 (m, 1H), 7.10-6.78 (m, 6H), 6.36 (s, 1H), 4.71-4.54 (m, 1H), 4.34-4.16 (m, 1H), 3.96-3.73 (m, 2H), 2.97-2.88 (m, 1H), 2.87-2.79 (m, 1H), 2.54-2.33 (m, 2H), 2.11-1.94 (m, 2H), 1.94-1.78 ppm (m, 2H). ¹³C NMR (101 MHz, Chloroform-d) δ = 162.53, 160.95, 158.45, 155.35, 153.00, 152.91, 147.42, 145.26, 145.15, 137.24, 132.52, 132.47, 131.49, 131.40, 125.91, 125.87, 125.14, 124.93, 124.42, 124.38, 122.37, 122.30, 118.81, 118.79, 116.84, 116.66, 114.86, 114.64, 114.07, 111.71, 109.35, 75.00, 58.81, 47.48, 46.29, 42.97, 31.33, 31.23 ppm. |
| 31 | ¹H NMR (400 MHz, Chloroform-d) δ = 8.80 (s, 1H), 7.38-7.30 (m, 1H), 7.26-7.20 (m, 1H), 7.09-7.02 (m, 1H), 6.94 (t, J = 54.2 Hz, 1H), 6.44-6.35 (m, 3H), 6.31 (s, 1H), 4.68-4.50 (m, 1H), 4.34-4.18 (m, 1H), 3.86-3.78 (m, 2H), 2.93-2.74 (m, 2H), 2.51-2.41 (m, 2H), 2.12-1.92 (m, 2H), 1.91-1.74 ppm (m, 2H). ¹³C NMR (101 MHz, Chloroform-d) δ = 165.18, 165.03, 162.73, 162.58, 162.52, 160.96, 159.35, 158.46, 153.04, 147.50, 137.16, 132.53, 132.47, 131.51, 131.42, 125.92, 125.88, 125.12, 124.91, 114.85, 114.64, 114.11, 111.75, 109.39, 99.65, 99.57, 99.45, 99.37, 96.87, 96.61, 96.35, 72.95, 58.92, 47.17, 46.33, 42.99, 30.90, 30.84 ppm. |
| 32 | ¹H NMR (400 MHz, Methanol-d₄) δ = 9.05 (s, 1H), 8.88 (dd, J = 4.3, 1.7 Hz, 1H), 8.61 (ddd, J = 8.6, 1.7, 0.8 Hz, 1H), 8.12 (dt, J = 8.5, 1.1 Hz, 1H), 7.78 (dd, J = 8.5, 7.1 Hz, 1H), 7.67 (dd, J = 7.1, 1.2 Hz, 1H), 7.57 (dd, J = 8.7, 4.3 Hz, 1H), 7.42 (td, J = 7.5, 1.9 Hz, 1H), 7.37-7.26 (m, 1H), 7.22-6.89 (m, 3H), 4.64-4.59 (m, 1H), 4.59 (s, 2H), 4.14-3.99 (m, 1H), 3.74-3.62 (m, 1H), 3.55-3.44 (m, 1H), 3.07-2.95 (m, 1H), 2.94-2.84 (m, 1H), 2.44-2.33 (m, 2H), 2.06-1.91 (m, 2H), 1.80-1.61 ppm (m, 2H). ¹³C NMR (101 MHz, Methanol-d₄) δ = 170.81, 163.41, 160.97, 155.76, 151.74, 148.66, 148.37, 140.57, 136.08, 135.68, 131.78, 131.41, 131.37, 130.66, 130.58, 130.07, 127.33, 127.10, 126.96, 126.93, 125.24, 125.21, 123.15, 116.15, 115.94, 114.23, 111.88, 109.54, 75.86, 64.48, 64.44, 61.07, 48.45, 44.58, 32.57, 32.45 ppm. |
| 33 | ¹H NMR (400 MHz, Chloroform-d) δ = 8.96 (dd, J = 4.2, 1.7 Hz, 1H), 8.78 (s, 1H), 8.72 (ddd, J = 8.6, 1.8, 0.9 Hz, 1H), 8.21 (dt, J = 8.4, 1.1 Hz, 1H), 7.71 (dd, J = 8.4, 7.1 Hz, 1H), 7.64 (d, J = 7.1 Hz, 1H), 7.46 (dd, J = 8.6, 4.2 Hz, 1H), 7.22-7.06 (m, 2H), 7.04-6.97 (m, 1H), 6.93 (t, J = 54.1 Hz, 1H), 6.48 (s, 1H), 4.68-4.56 (m, 1H), 4.44 (s, 2H), 4.02-3.88 (m, 1H), 3.90-3.76 (m, 1H), 3.47-3.33 (m, 1H), 3.00-2.88 (m, 1H), 2.89-2.78 (m, 1H), 2.44-2.25 (m, 2H), 2.02-1.89 (m, 2H), 1.78-1.59 ppm (m, 2H). ¹³C NMR (101 MHz, Chloroform-d) δ = 168.29, 153.03, 151.16, 148.46, 138.08, 135.88, 134.23, 133.89, 132.81, 128.39, 125.97, 125.45, 123.28, 123.24, 123.21, 123.18, 122.17, 117.33, 117.16, 116.51, 116.34, 114.20, 111.85, 109.48, 74.27, 68.82, 59.37, 48.31, 47.00, 43.12, 31.65, 31.54 ppm. |
| 34 | ¹H NMR (400 MHz, Methanol-d₄) δ = 9.07 (d, J = 0.7 Hz, 1H), 8.89 (dd, J = 4.3, 1.7 Hz, 1H), 8.62 (ddd, J = 8.6, 1.7, 0.9 Hz, 1H), 8.13 (dt, J = 8.5, 1.1 Hz, 1H), 7.79 (dd, J = 8.5, 7.1 Hz, 1H), 7.68 (dd, J = 7.1, 1.2 Hz, 1H), 7.58 (dd, J = 8.7, 4.3 Hz, 1H), 7.06 (t, J = 53.6 Hz, 1H), 7.00-6.92 (m, 2H), 6.92-6.85 (m, 2H), 4.69-4.60 (m, 1H), 4.35-4.25 (m, 1H), 4.18-4.06 (m, 1H), 3.74-3.64 (m, 1H), 3.02-2.93 (m, 1H), 2.93-2.83 (m, 1H), 2.59-2.45 (m, 2H), 2.10-1.96 (m, 2H), 1.91-1.71 ppm (m, 2H). ¹³C NMR (101 MHz, Methanol-d₄) δ = 170.83, 159.91, 157.55, 155.79, 154.94, 154.92, 151.76, 148.67, 148.42, 148.18, 140.57, 140.53, 136.07, 135.67, 131.80, 130.07, 127.34, 126.94, 123.14, 118.67, 118.59, 116.81, 116.58, 114.28, 111.93, 109.58, 74.39, 61.12, 48.18, 44.58, 32.20, 32.13 ppm. |
| 35 | ¹H NMR (400 MHz, Methanol-d₄) δ = 9.07 (s, 1H), 8.89 (dd, J = 4.3, 1.7 Hz, 1H), 8.62 (ddd, J = 8.6, 1.7, 0.9 Hz, 1H), 8.13 (dt, J = 8.5, 1.1 Hz, 1H), 7.79 (dd, J = 8.6, 7.1 Hz, 1H), 7.68 (dd, J = 7.1, 1.2 Hz, 1H), 7.58 (dd, J = 8.6, 4.3 Hz, 1H), 7.26-7.18 (m, 2H), 7.06 (t, J = 53.6 Hz, 1H), 6.92-6.84 (m, 2H), 4.70-4.61 (m, 1H), 4.45-4.30 (m, 1H), 4.13-4.07 (m, 1H), 3.75-3.64 (m, 1H), 3.03-2.93 (m, 1H), 2.92-2.83 (m, 1H), 2.60-2.43 (m, 2H), 2.09-1.95 (m, 2H), 1.88-1.71 ppm (m, 2H). ¹³C NMR (101 MHz, Methanol-d₄) δ = 170.83, 157.54, 155.80, 151.76, 148.67, 148.43, 148.19, 140.55, 136.07, 135.67, 131.81, 130.37, 130.08, 127.34, 126.94, 126.60, 123.15, 118.55, 114.28, 111.94, 109.59, 73.87, 61.12, 48.15, 44.57, 32.11, 32.06, 30.58 ppm. |
| 36 | ¹H NMR (400 MHz, Methanol-d₄) δ = 9.07 (s, 1H), 8.90 (dd, J = 4.3, 1.7 Hz, 1H), 8.62 (ddd, J = 8.6, 1.7, 0.9 Hz, 1H), 8.13 (dt, J = 8.6, 1.1 Hz, 1H), 7.79 (dd, J = 8.5, 7.1 Hz, 1H), 7.68 (dd, J = 7.1, 1.2 Hz, 1H), 7.58 (dd, J = 8.6, 4.3 Hz, 1H), 7.29-7.16 (m, 1H), 7.07 (t, J = 53.6 Hz, 1H), 6.75-6.56 (m, 3H), 4.70-4.60 (m, 1H), 4.44-4.35 (m, 1H), 4.15-4.06 (m, 1H), 3.75-3.66 (m, 1H), 3.03-2.93 (m, 1H), 2.93-2.83 (m, 1H), 2.63-2.48 (m, 2H), 2.12-1.97 (m, 2H), 1.94-1.72 ppm (m, 2H). ¹³C NMR (101 MHz, Methanol-d₄) δ = 170.84, 166.34, 163.92, 160.38, 160.27, 155.81, 151.76, 148.67, 148.42, 148.18, 140.62, 136.07, 135.67, 131.81, 131.56, 131.46, 130.08, 127.34, 126.94, 123.15, 114.28, 112.80, 112.70, 111.93, 109.59, 108.40, 108.19, 104.47, 104.22, 73.75, 61.13, 48.17, 44.57, 32.08, 32.03 ppm. |
| 37 | ¹H NMR (400 MHz, Chloroform-d) δ = 8.96 (dd, J = 4.2, 1.7 Hz, 1H), 8.79 (s, 1H), 8.72 (ddd, J = 8.7, 1.7, 0.9 Hz, 1H), 8.21 (dt, J = 8.4, 1.1 Hz, 1H), 7.72 (dd, J = 8.4, 7.1 Hz, 1H), 7.65 (d, J = 7.1 Hz, 1H), 7.47 (dd, J = 8.6, 4.2 Hz, 1H), 7.11-6.77 (m, 5H), 6.48 (s, 1H), 4.73-4.60 (m, 1H), 4.37-4.24 (m, 1H), 4.03-3.89 (m, 1H), 3.92-3.80 (m, 1H), 3.09-2.93 (m, 1H), 2.92-2.84 (m, 1H), 2.52-2.41 (m, 2H), 2.08-1.96 (m, 2H), 1.96-1.79 ppm (m, 2H). ¹³C NMR (101 MHz, Chloroform-d) δ = 168.31, 155.39, 153.06, 152.95, 151.16, 148.46, 145.22, 145.11, 138.19, 134.23, 133.89, |

-continued

| Compound | $^1$H-NMR 400/$^{13}$C-NMR 101 |
|---|---|
| | 132.82, 128.41, 125.97, 125.46, 124.44, 124.40, 122.46, 122.39, 122.18, 118.90, 118.88, 116.88, 116.69, 114.22, 111.86, 109.50, 74.89, 59.42, 47.66, 46.75, 43.14, 31.38, 31.29 ppm. |
| 38 | $^1$H NMR (400 MHz, Chloroform-d) δ = 8.96 (dd, J = 4.2, 1.7 Hz, 1H), 8.81 (s, 1H), 8.71 (ddd, J = 8.6, 1.8, 0.9 Hz, 1H), 8.21 (dt, J = 8.4, 1.1 Hz, 1H), 7.71 (dd, J = 8.4, 7.1 Hz, 1H), 7.64 (d, J = 7.0 Hz, 1H), 7.47 (dd, J = 8.6, 4.2 Hz, 1H), 6.95 (t, J = 54.2 Hz, 1H), 6.44 (s, 1H), 6.41-6.32 (m, 3H), 4.72-4.61 (m, 1H), 4.31-4.20 (m, 1H), 4.07-3.92 (m, 1H), 3.92-3.79 (m, 1H), 2.96-2.79 (m, 2H), 2.60-2.45 (m, 2H), 2.10-1.93 (m, 2H), 1.92-1.74 ppm (m, 2H). $^{13}$C NMR (101 MHz, Chloroform-d) δ = 168.32, 165.19, 165.03, 162.74, 162.58, 159.44, 159.30, 159.17, 153.15, 151.16, 148.44, 138.08, 134.22, 133.87, 132.82, 128.38, 125.97, 125.46, 122.18, 114.25, 111.89, 109.53, 99.66, 99.58, 99.47, 99.39, 96.93, 96.67, 96.42, 72.79, 59.52, 47.43, 46.79, 43.16, 30.90 ppm. |

Pharmacological Examples

The compounds of the invention were found to be active on a human P2X7 channel assay by automated patch-clamp.

In order to directly monitor the block of P2X7 channel, an electrophysiological assay was developed and implemented on the QPatch16X automated electrophysiology instrument.

HEK-293 cells expressing the P2X7 channels were cultured in modified EMEM.

72 hours before experiment, 5 million cells were seeded onto T225 flasks. Just before the experiment cells were washed twice, detached from the flask with trypsin-EDTA, re-suspended in the suspension solution and placed on the QPatch 16x.

The compounds (20 mM in a 100% DMSO) stored at −20° C. were prepared the day of the experiment (a first dilution 1:20 in 100% DMSO to prepare a 1 mM stock solution, then a 1 microM solution in external solution+a serial dilution 1:10).

The standard whole-cell voltage clamp experiments were performed at room temperature. For these experiments the multihole technology was used and the data were sampled at 2 KHz.

The intracellular solution contained (mM) 135 CsF, 10 NaCl, 1 EGTA, 10 HEPES, (pH 7.2 with CsOH) whereas the extracellular contained (mM) 145 NaCl, 4 KCl, 0.5 $MgCl_2$, 1 $CaCl_2$, 10 HEPES, 10 Glc (pH 7.4 with NaOH).

After establishment of the seal and the passage in the whole cell configuration, the cells were held at −80 mV. The P2XR7 current was evoked by applying 100 microM of BzATP alone (4 times) and then in the presence increasing concentrations of the compound under investigation (1, 10, 100 and 1000 nM).

The pre-incubation periods 5 to 8 contain increasing concentrations of the compound of interest (1, 10, 100 and 1000 nM), as illustrated in FIGURE.

The maximal inward current evoked by BzATP in absence or presence of increasing concentrations of the compounds under investigation was measured and normalized. The potential modulatory effect was measured as % of control and as $IC_{50}$ determined fitting the dose-response curves data with the following equation:

$$Y=100/(1+10\char`\^((Log\ IC50-X)*HillSlope))$$

where:
X: log of concentration
Y: normalized response, 100% down to 0%, decreasing as X increases.

$LogIC_{50}$: same log units as X
HillSlope: slope factor or HS, unitless

TABLE 3

| Compound | hP2X7 ($IC_{50}$; nM) | ±SEM |
|---|---|---|
| 1 | 44.96 | 7.73 |
| 3 | 5.95 | 1.66 |
| 4 | 28.14 | 3.73 |
| 5 | 35.12 | 5.08 |
| 7 | 51.50 | 16.41 |
| 9 | 23.59 | 3.83 |
| 10 | 42.89 | 7.22 |
| 11 | 30.65 | 1.13 |
| 12 | 25.84 | 3.16 |
| 13 | 42.06 | 11.40 |
| 15 | 11.55 | 3.49 |
| 17 | 32.91 | 1.90 |
| 18 | 36.85 | 8.49 |
| 19 | 23.91 | 5.37 |
| 21 | 26.35 | 1.08 |
| 22 | 30.17 | 0.78 |
| 24 | 57.86 | 8.03 |
| 29 | 28.94 | 6.10 |
| 30 | 40.69 | 11.25 |
| 33 | 56.18 | 2.60 |
| 34 | 39.66 | 8.42 |
| 37 | 43.19 | 2.34 |

The compounds of the invention were found to be rat P2X7 inhibitors using a Screen Quest™ Fluo-8 No Wash Calcium Assay Kit.

$Ca^{2+}$ influx was measured in HEK-293 cells stably transfected with the receptor using Screen Quest™ Fluo-8 No Wash Calcium Assay Kit (AAt Bioquest®). Briefly, once inside the cells, the lipophilic blocking groups of Fluo-8 are cleaved by non-specific cell esterases, resulting in a negatively-charged fluorescent-dye that stays inside cells. Its fluorescence increases upon binding to calcium. When HEK-293/P2X7 cells were stimulated with BzATP, $Ca^{2+}$ entered the cells and the fluorescence of Fluo-8 NW increaseed. The dye absorption spectrum was compatible with excitation at 488 nm by argon laser sources and its emission wavelength was in the range of 515-575 nm.

To routinely test the compounds, HEK-293 cells stably transfected with rat P2X7R were seeded overnight in growth medium at 10000, 15000 or 20000 cells/well in 384-well plate, according to the level of response after thawing. 24 hours later, the medium was removed and the cells were pre-loaded at RT for 1 hour with 20 μL/w of Fluo-8 NW prepared in Tyrode 0.3 mM $Ca^{2+}/Mg^{2+}$-free. Compounds of the invention were tested at 8 concentrations (4 replicates for each concentration): 10-3.16-1-0.316-0.1-0.0316-0.01 and 0.00316 μM, in the same plate.

Compounds were tested at FLIPRTETRA according to the following method:
first injection at FLIPRTETRA of 10 μL of 3× test compound (in Tyrode's buffer 0.3 mM $Ca^{2+}/Mg^{2+}$-free+DMSO 0.5% final concentration)
5' incubation
second injection at FLIPRTETRA of 15 μL of 3× BzATP at ~ECK) (in Tyrode's buffer 0.3 mM $Ca^{2+}/Mg^{2+}$-free+ BSA 0.0003% final concentration)
Fluorescence recording for 3'
Between one plate and the following, tips were extensively washed with water, then with 100% DMSO and finally with water to avoid carry-over inside the tips.

The effect of the test compounds was measured as percent inhibition vs a reference antagonist and $IC_{50}$ values were calculated accordingly.

TABLE 4

| Compound | rP2X7 (IC$_{50}$; nM) |
|---|---|
| 1 | 1041 |
| 2 | 971 |
| 3 | 373 |
| 4 | 953 |
| 5 | 506 |
| 6 | 1165 |
| 7 | 709 |
| 8 | 1308 |
| 9 | 402 |
| 10 | 583 |
| 11 | 594 |
| 12 | 380 |
| 13 | 371 |
| 14 | 1118 |
| 15 | 288 |
| 16 | 762 |
| 17 | 432 |
| 18 | 374 |
| 19 | 582 |
| 20 | 808 |
| 21 | 268 |
| 22 | 355 |
| 23 | 631 |
| 24 | 201 |
| 25 | 252 |
| 26 | 578 |
| 27 | 1214 |
| 28 | 2022 |
| 29 | 441 |
| 30 | 329 |
| 31 | 458 |
| 32 | 251 |
| 33 | 182 |
| 34 | 144 |
| 35 | 323 |
| 36 | 295 |
| 37 | 133 |
| 38 | 216 |

Compounds of the present invention were found to be unexpectedly more potent than a very close Example of WO2015/118019 as reported in the table 5.

TABLE 5

| Compound | rP2X7 (IC$_{50}$; nM) |
|---|---|
| 21 | 268 |
| 24 | 201 |
| 34 | 144 |
| 37 | 133 |
| Compound 59 of WO2015118019 | 1019 |

In vitro evaluation of test compounds for metabolic stability using Human liver Microsomes.

Test System Human (Mouse) Liver Microsomes
Test compound concentration: 1 µM
Time Points: 0, 5, 10, 30 and 60 minutes
Final Protein concentration: 1 mg/mL
Number of Replicates: Two
Potassium Phosphate Buffer pH 7.4 100 mM
End Point: % Remaining of Test compound, Half life, Clint
Bioanalysis by LC-MS/MS
Preparation and Dilution of Test Compound:
10 mM stock solution of test compound were prepared in DMSO and dilute with water: acetonitrile (1:1) to a concentration of 1 mM. Working concentration of 100 µM were prepared by further dilution with water: acetonitrile (1: 1).

Preparation of Potassium Phosphate buffer pH 7.4:
100 mL of Milli Q water will be added to K2HPO$_4$ (1.398 g) and KH2PO4 (0.27 g) to get final pH 7.4.

Assay Procedure:
Preincubation mixture: 2.5 µL Test Cpd.+75 µL Liver microsomes@3.33 mg/mL+85 µL of 100 mM potassium phosphate buffer (Preincubate for 10 min @37° C.)

60 min w/o cofactor: 32.5 µL of Preincubation mixture+ 17.5 µL of 100 mM potassium phosphate buffer (Incubate for 60 min@37° C.)

0 min sample: 16.25 µL of Preincubation mixture+200 µL of acetonitrile containing internal standard+8.75 µL of cofactor Incubation mixture 62 µL of cofactor (2.5 mM)+ Remaining incubation mixture (Incubated for 60 min@37° C.).

Sample preparation: 25 µL incubation mixture+200 µL of acetonitrile containing internal standard+Vortex 5 min@1200 rpm+Centrifuge 10 min@4000 rpm. Dilute supernatant 2 fold with water and injected on LC-MS/MS.

Bioanalysis: LC-MS/MS method LC generic gradient conditions will be used and the details will be provided in the report.

Calculation: % remaining of the test substance=[Peak Area at time in min/Peak Area at 0 min]*100 K$_{el}$: Slope obtained from the plot of Log % remaining vs. time (min)
Half life: $t_{1/2}$(min)=0.693/Kel $$\text{Intrinsic clearance (µl/min/mg)} = ABS(K_{el}/\text{Protein Concentration})*1000$$

Examples of the present invention were unexpectedly found to be 2-4 times more stable in human liver microsomal stability tests than a very similar compound exemplified in WO2015118019 as reported in the table 6.

TABLE 6

| Compound | Human Liver Microsomal Clearance (CL$_i$; µg/min/mg protein) |
|---|---|
| 11 | 59.41 |
| 19 | 71.12 |
| 22 | 93.44 |
| Compound 59 of WO2015/118019 | 213.46 |

The invention claimed is:

1. A compound of the following formula (I) or a pharmaceutically acceptable salt thereof:

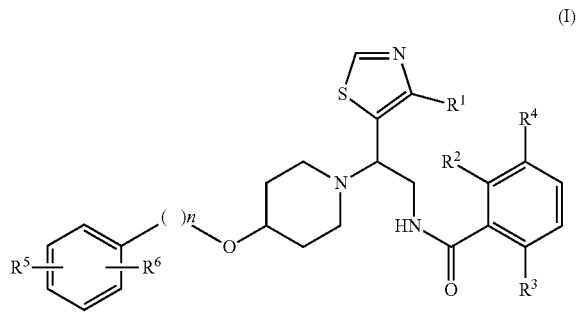

(I)

including any stereochemically isomeric form thereof, wherein:

n is 0 or 1;

R$^1$ is C1-C4 alkyl (optionally substituted with hydroxyl or halogen);

each of R$^2$, R$^3$, and R$^4$ is independently hydrogen, halogen, or the R$^2$ and R$^4$ groups, taken together, form a six membered heterocyclic ring containing a nitrogen atom, provided that at least one of R$^2$, R$^3$, and R$^4$ is not hydrogen;

each of R$^5$ and R$^6$ is hydrogen or halogen provided that at least one of R$^5$ and R$^6$ is halogen.

2. The compound of Formula (I) according to claim 1 or a pharmaceutically acceptable salt thereof including any stereochemically isomeric form thereof, wherein:

n is 0 or 1;

R$^1$ is methyl, or difluoromethyl;

each of R$^2$, R$^3$, and R$^4$ independently is hydrogen, fluorine, chlorine or the R$^2$ and R$^4$ groups, taken together, form a six membered heterocyclic ring containing a nitrogen atom provided that at least one of R$^2$, R$^3$, and R$^4$ is not hydrogen;

each of R$^5$ and R$^6$ is hydrogen, fluorine or chlorine provided that at least one of R$^5$ and R$^6$ is halogen.

3. The compound of formula (I) according to claim 1 or a pharmaceutically acceptable salt thereof including any stereochemically isomeric form thereof, wherein:

n is 0 or 1;

R$^1$ is methyl, or difluoromethyl;

each of R$^2$, R$^3$, and R$^4$ independently is hydrogen, fluorine or chlorine, provided that at least one of R$^2$, R$^3$, and R$^4$ is not hydrogen;

each of R$^5$ and R$^6$ is hydrogen, fluorine or chlorine provided that at least one of R$^5$ and R$^6$ is halogen.

4. The compound of formula (I) according to claim 1 or a pharmaceutically acceptable salt thereof including any stereochemically isomeric form thereof, wherein:

n is 0 or 1;

R$^1$ is methyl, or difluoromethyl;

R$^3$ is hydrogen and the R$^2$ and R$^4$ groups, taken together, form a six membered heterocyclic ring, wherein the six membered heterocyclic ring together the phenyl group form a quinoline ring.

5. A compound of formula (I) according to claim 1, or a pharmaceutically acceptable salt thereof including any stereochemically isomeric form thereof, selected from the group consisting of:

2-chloro-6-fluoro-N-(2-{4-[(4-fluorophenyl)methoxy]piperidin-l-yl}-2-(4-methyl -1,3-thiazol-5-yl)ethyl)benzamide, 2-chloro-N-(2-{4-[(4-chlorophenyl)methoxy]piperidin-1-yl}-2-(4-methyl -1,3-thiazol-5-yl)ethyl)-6-fluorobenzamide, 2-chloro-6-fluoro-N-(2-{4-[(3-fluorophenyl)methoxy]piperidin-1-yl}-2-(4-methyl-1,3-thiazol-5-yl)ethyl)benzamide, 2-chloro-6-fluoro-N-(2-{4-[(2-fluorophenyl)methoxy]piperidin-1-yl}-2-(4-methyl-1,3-thiazol-5-yl)ethyl)benzamide, 2-chloro-N-(2-{4-[(3,5-difluorophenyl)methoxy]piperidin-1-yl}-2-(4-methyl -1,3-thiazol-5-yl)ethyl)-6-fluorobenzamide, 2-chloro-N-(2-{4-[(3,4-difluorophenyl)methoxy]piperidin-1-yl}-2-(4-methyl -1,3-thiazol-5-yl)ethyl)-6-fluorobenzamide, 2-chloro-6-fluoro-N-{2-[4-(4-fluorophenoxy)piperidin-1-yl]-2-(4-methyl -1,3-thiazol-5-yl)ethyl}benzamide, 2-chloro-N-{2-[4-(4-chlorophenoxy)piperidin-1-yl]-2-(4-methyl -1,3-thiazol-5-yl)ethyl}-6-fluorobenzamide, 2-chloro-6-fluoro-N-{2-[4-(3-fluorophenoxy)piperidin-1-yl]-2-(4-methyl -1,3-thiazol-5-yl)ethyl}benzamide, 2-chloro-6-fluoro-N-{2-[4-(2-fluorophenoxy)piperidin-1-yl]-2-(4-methyl -1,3-thiazol-5-yl)ethyl}benzamide, 2-chloro-N-{2-[4-(3,5-difluorophenoxy)piperidin-1-yl]-2-(4-methyl-1,3-thiazol-5-yl)ethyl }-6-fluorobenzamide, 2-chloro-N-{2-[4-(3,4-difluorophenoxy)piperidin-1-yl]-2-(4-methyl-1,3-thiazol-5-yl)ethyl}-6-fluorobenzamide, N-(2-{4-[(4-fluorophenyl)methoxy]piperidin-1-yl}-2-(4-methyl-1,3-thiazol-5-yl)ethyl)quinoline-5-carboxamid, N-(2-{4-[(4-chlorophenyl)methoxy]piperidin-1-yl}-2-(4-methyl-1,3-thiazol-5-yl)ethyl)quinoline-5-carboxamid, N-(2-{4-[(3-fluorophenyl)methoxy]piperidin-1-yl}-2-(4-methyl-1,3-thiazol-5-yl)ethyl)quinoline-5-carboxamid, N-(2-{4-[(2-fluorophenyl)methoxy]piperidin-1-yl}-2-(4-methyl-1,3-thiazol-5-yl)ethyl)quinoline-5-carboxamid, N-(2-{4-[(3,5-difluorophenyl)methoxy]piperidin-1-yl}-2-(4-methyl-1,3-thiazol-5-yl)ethyl)quinoline-5-carboxamid, N-(2-{4-[(3,4-difluorophenyl)methoxy]piperidin-1-yl}-2-(4-methyl-1,3-thiazol-5-yl)ethyl)quinoline-5-carboxamid, N-{2-[4-(4-fluorophenoxy)piperidin-1-yl]-2-(4-methyl-1,3-thiazol-5-yl)ethyl}quinoline-5-carboxamide, N-{2-[4-(4-chlorophenoxy)piperidin-1-yl]-2-(4-methyl-1,3-thiazol-5-yl)ethyl}quinoline-5-carboxamide, N-{2-[4-(3-fluorophenoxy)piperidin-1-yl]-2-(4-methyl-1,3-thiazol-5-yl)ethyl}quinoline-5-carboxamide, N-{2-[4-(2-fluorophenoxy)piperidin-1-yl]-2-(4-methyl-1,3-thiazol-5-yl)ethyl}quinoline-5-carboxamide, N-{2-[4-(3,5-difluorophenoxy)piperidin-1-yl]-2-(4-methyl-1,3-thiazol-5-yl)ethyl}quinoline-5-carboxamide, N-{2-[4-(3,4-difluorophenoxy)piperidin-1-yl]-2-(4-methyl-1,3-thiazol-5-yl)ethyl}quinoline-5-carboxamide, 2-chloro-N-{2-[4-(difluoromethyl)-1,3-thiazol-5-yl]-2-{4-[(2-fluorophenyl) methoxy]piperidin-1-yl}ethyl}-6-fluorobenzamide 2-chloro-N-{2-[4-(difluoromethyl)-1,3-thiazol-5-yl]-2-{4-[(3,5-difluorophenyl) methoxy]piperidin-1-yl}ethyl}-6-fluorobenzamide 2-chloro-N-{2-[4-(difluoromethyl)-1,3-thiazol-5-yl]-2-{4-[(3,4-difluorophenyl) methoxy]piperidin-1-yl}ethyl}-6-fluorobenzamide 2-chloro-N-{2-[4-(4-chlorophenoxy)piperidin-1-yl]-2-[4-(difluoromethyl) -1,3-thiazol-5-yl]ethyl}-6-fluorobenzamide 2-chloro-N-{2-[4-(difluoromethyl)-1,3-thiazol-5-yl]-2-[4-(3-fluorophenoxy)piperidin-1-yl]ethyl}-6-fluorobenzamide 2-chloro-N-{2-[4-(difluoromethyl)-1,3-thiazol-5-yl]-2-[4-(2-fluorophenoxy)piperidin-1-yl]ethyl}-6-fluorobenzamide 2-chloro-N-{2-[4-(difluoromethyl)-1,3-thiazol-5-yl]-2-[4-(3,5-difluorophenoxy)piperidin-1-yl]ethyl}-6-fluorobenzamide N-{2-[4(difluoromethyl)-1,3-thiazol-5-yl]-2-{4-[(2-fluorophenyl) methoxy]piperidin-1-yl}ethyl}quinoline-5-carboxamide N-{2-[4-(difluoromethyl)-1,3-thiazol-5-yl]-2{4-[(3,4-difluorophenyl)methoxy]piperidin-1-yl}ethyl}quinoline-5-carboxamide N-{2-[4-(difluoromethyl)-1,3-thiazol-5-yl]-2-[4-(4-fluorophenoxy)piperidin-1-yl]ethyl}quinoline-5-carboxamide N-{2-[4-(4-chlorophenoxy)piperidin-1-yl]-2-[4-(difluoromethyl)-1,3-thiazol-5-yl]ethyl}quinoline-5-carboxamide N-{2-[4-(difluoromethyl)-1,3-thiazol-5-yl]-2-[4-(3-fluorophenoxy) piperidin-1-yl] ethyl } quinoline-5-carboxamide N-{2-[4-(difluoromethyl)-1,3-thiazol-5-yl]-2-[4-(2-fluorophenoxy) piperidin-1-yl] ethyl } quinoline-5-carboxamide, and N-{2-[4-(difluoromethyl)-1,3-thiazol-5-yl]-2-[4-(3,5-difluorophenoxy) piperidin-1-yl]ethyl}quinoline-5-carboxamide.

6. A process for preparing a compound of formula (I) as defined in claim 1 comprising the steps of:

i) reacting a compound of formula (II):

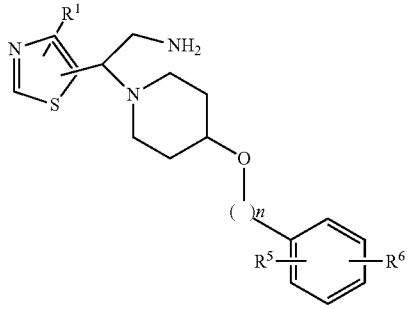

(II)

wherein the meanings of n, R1, R5 and R6 are as defined above, with a compound of formula (III)

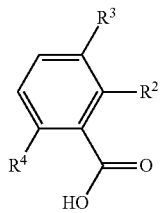

(III)

wherein the meanings of R2, R3 and R4 are as defined above; or with a compound of Formula (IIIa):

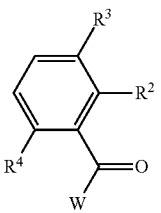

(IIIa)

wherein the meanings of R2, R3 and R4 are as defined above; and W is a suitable leaving group;

and optionally converting the obtained compound of formula (I) into a salt thereof, and/or preparing stereochemically isomeric forms thereof.

7. A pharmaceutical formulation comprising a compound of formula (I) according to claim 1, or a pharmaceutically acceptable salt thereof including any stereochemically isomeric form thereof, and a pharmaceutically acceptable diluent and/or carrier.

* * * * *